(12) United States Patent
Sexton

(10) Patent No.: US 10,485,707 B2
(45) Date of Patent: Nov. 26, 2019

(54) SYSTEMS AND METHODS FOR TISSUE HEALING

(71) Applicant: ATOMIC MEDICAL INNOVATIONS, INC., Buffalo, NY (US)

(72) Inventor: Jay Sexton, Buffalo, NY (US)

(73) Assignee: Atomic Medical Innovations, Inc., Tucson, AZ (US)

( * ) Notice: Subject to any disclaimer, the term of this patent is extended or adjusted under 35 U.S.C. 154(b) by 275 days.

(21) Appl. No.: 15/118,839

(22) PCT Filed: Feb. 13, 2015

(86) PCT No.: PCT/US2015/015968
§ 371 (c)(1),
(2) Date: Aug. 12, 2016

(87) PCT Pub. No.: WO2015/123609
PCT Pub. Date: Aug. 20, 2015

(65) Prior Publication Data
US 2017/0049627 A1 Feb. 23, 2017

Related U.S. Application Data

(60) Provisional application No. 61/940,245, filed on Feb. 14, 2014.

(51) Int. Cl.
*A61M 1/00* (2006.01)
*A61F 13/02* (2006.01)
*A61F 13/00* (2006.01)

(52) U.S. Cl.
CPC ...... *A61F 13/00068* (2013.01); *A61F 13/022* (2013.01); *A61F 13/0216* (2013.01); *A61F 13/0223* (2013.01); *A61M 1/0088* (2013.01)

(58) Field of Classification Search
CPC ............ A61F 13/00068; A61F 13/0216; A61F 13/022; A61F 13/0223; A61M 1/0088; A61M 1/009
(Continued)

(56) References Cited

U.S. PATENT DOCUMENTS 3,978,855 A * 9/1976 McRae ................. A61L 15/425
602/46
5,636,643 A * 6/1997 Argenta .............. A61M 1/0088
128/897
(Continued)

FOREIGN PATENT DOCUMENTS

CN  1438904 A  8/2003
CN  1741824 A  3/2006
(Continued)

OTHER PUBLICATIONS

International Search Report for PCT application No. PCT/US2015/015968 dated May 20, 2015 (2 pages).
(Continued)

*Primary Examiner* — Susan S Su
(74) *Attorney, Agent, or Firm* — Lewis Roca Rothgerber Christie LLP

(57) ABSTRACT

Systems, methods and devices are provided for use in a negative pressure wound therapy system for healing a wound in a patient. Various aspects may include an ester-based material adapted to be directly applied to the wound, such as a smooth muscle fistula, without substantially damaging tissue in the wound during dressing changes. The ester-based material may have an affinity for the wound bed surface and/or wound fluid. In addition various aspects may include a device adapted to close the wound, such as a smooth muscle fistula.

11 Claims, 14 Drawing Sheets

(58) Field of Classification Search
USPC .................. 604/304–308, 540, 541, 543
See application file for complete search history.

(56) References Cited

U.S. PATENT DOCUMENTS

| | | | |
|---|---|---|---|
| 2002/0115952 A1 | 8/2002 | Johnson et al. | |
| 2004/0030304 A1 | 2/2004 | Hunt | |
| 2007/0027414 A1* | 2/2007 | Hoffman | A61M 1/0088 602/2 |
| 2007/0185426 A1 | 8/2007 | Ambrosio | |
| 2008/0125687 A1* | 5/2008 | Flick | A61F 13/00063 602/48 |
| 2009/0069736 A1 | 3/2009 | Park | |
| 2009/0177133 A1* | 7/2009 | Kieswetter | A61F 13/00008 602/48 |
| 2009/0198167 A1 | 8/2009 | Ambrosio | |
| 2009/0204084 A1 | 8/2009 | Blott et al. | |
| 2009/0216168 A1 | 8/2009 | Eckstein | |
| 2010/0106106 A1 | 4/2010 | Heaton et al. | |
| 2010/0121229 A1* | 5/2010 | Argenta | A61B 17/00234 601/6 |
| 2010/0125258 A1 | 5/2010 | Coulthard | |
| 2011/0178451 A1 | 7/2011 | Robinson et al. | |
| 2011/0230809 A1 | 9/2011 | Manwaring | |
| 2012/0220963 A1 | 8/2012 | Hunt et al. | |
| 2013/0096520 A1 | 4/2013 | Lockwood et al. | |
| 2013/0102979 A1 | 4/2013 | Coultard et al. | |
| 2013/0131564 A1 | 5/2013 | Locke et al. | |
| 2013/0310809 A1 | 11/2013 | Armstrong et al. | |
| 2014/0236112 A1* | 8/2014 | Von Wolff | A61L 15/46 604/369 |
| 2016/0143786 A1* | 5/2016 | Bjork | A61L 15/32 604/307 |

FOREIGN PATENT DOCUMENTS

| | | |
|---|---|---|
| CN | 103120610 A | 5/2013 |
| CN | 102781382 B | 3/2016 |
| EP | 2572737 A1 | 3/2013 |
| JP | 2002291867 A | 10/2002 |
| JP | 2009508549 A | 3/2009 |
| JP | 2010516387 A | 5/2010 |
| JP | 2011510753 A | 4/2011 |
| JP | 2011125730 A | 6/2011 |
| JP | 2013517097 A | 5/2013 |
| RU | 2445947 C2 | 3/2012 |
| WO | WO0185248 A1 | 11/2001 |
| WO | WO2004039421 A1 | 5/2004 |
| WO | WO2008091521 A2 | 7/2008 |
| WO | WO2009/097534 A1 | 8/2009 |

OTHER PUBLICATIONS

Written Opinion for PCT application No. PCT/US2015/015968 dated May 20, 2015 (6 pages).
Extended European Search Report and European Search Opinion dated Aug. 25, 2017, issued in corresponding EP Application No. 15748570.7, 9 pps.
AU Examination Report No. 1 dated Nov. 7, 2018, issued in corresponding Appln. No. 2015218302.
CN Patent Office action dated Dec. 26, 2018, issued in corresponding Appln. No. 2018122101779670, with English translation.
EP Patent Office action dated Oct. 25, 2018, issued in corresponding Appln. No. 15748570.7.
RU Patent Office action dated Sep. 7, 2018, issued in corresponding Appln. No. 2016136672/14 (057576), with English translation.
JP Patent Office action dated Jan. 29, 2019, issued in Appln. No. 2016-569568, with English translation.

* cited by examiner

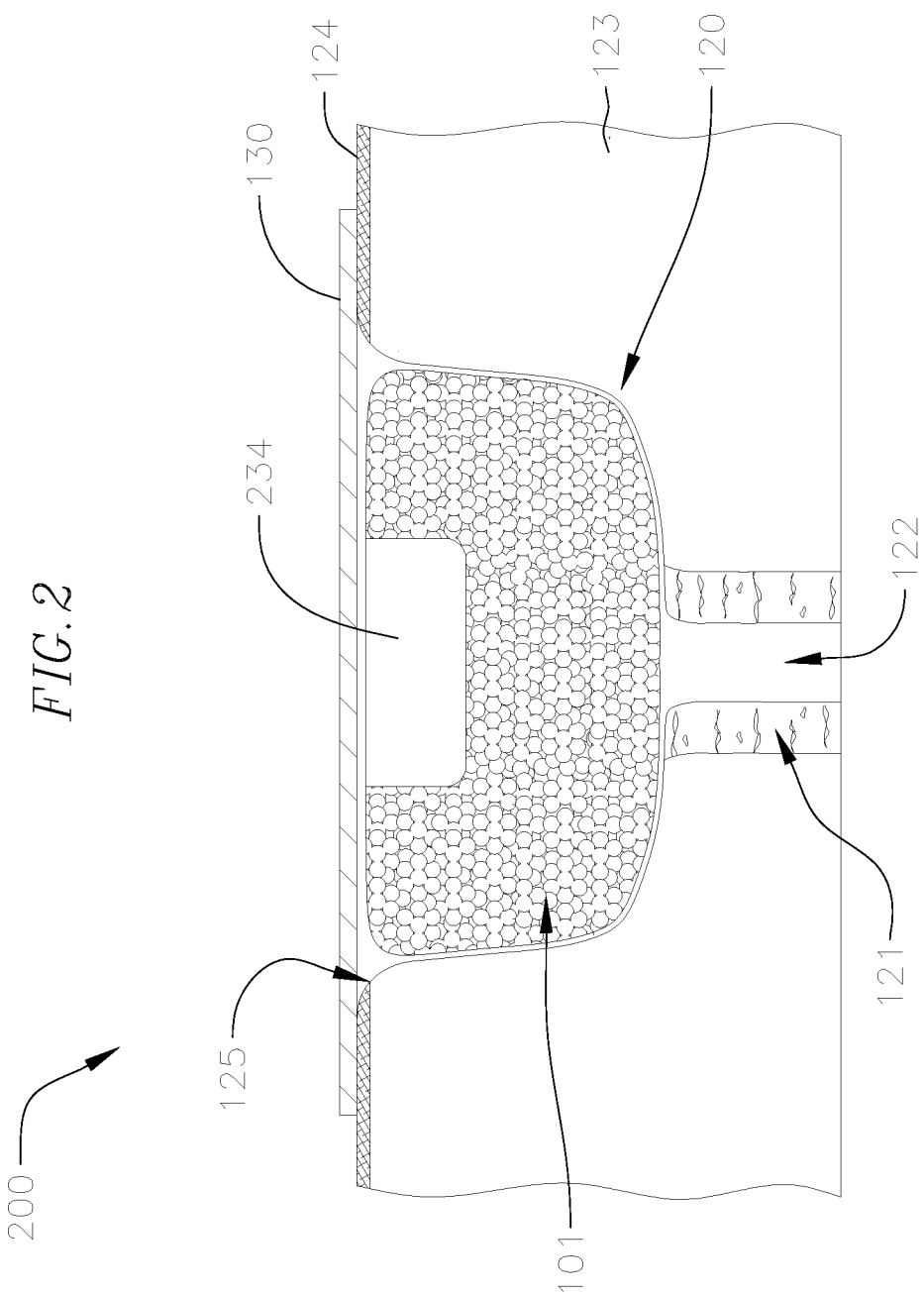

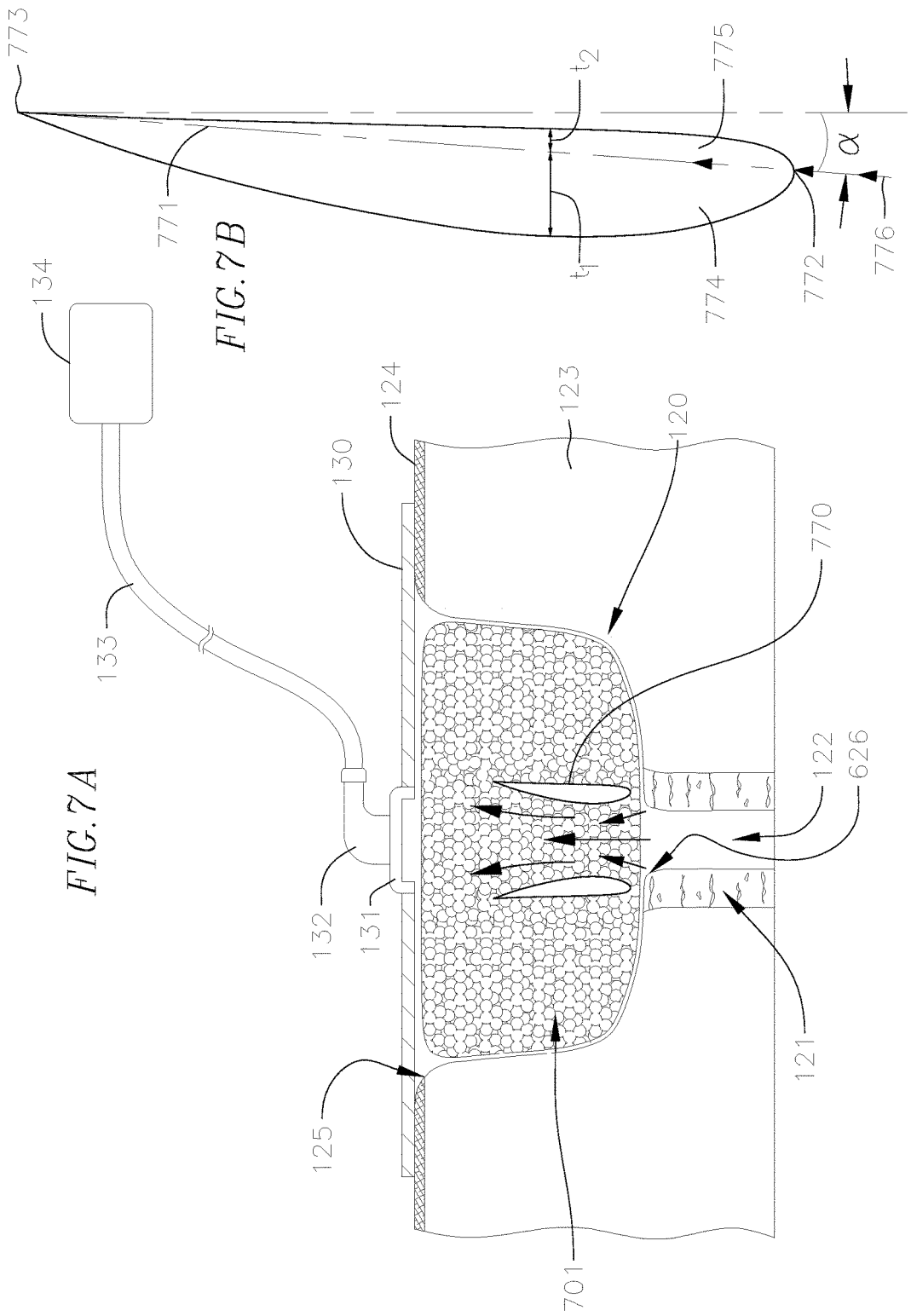

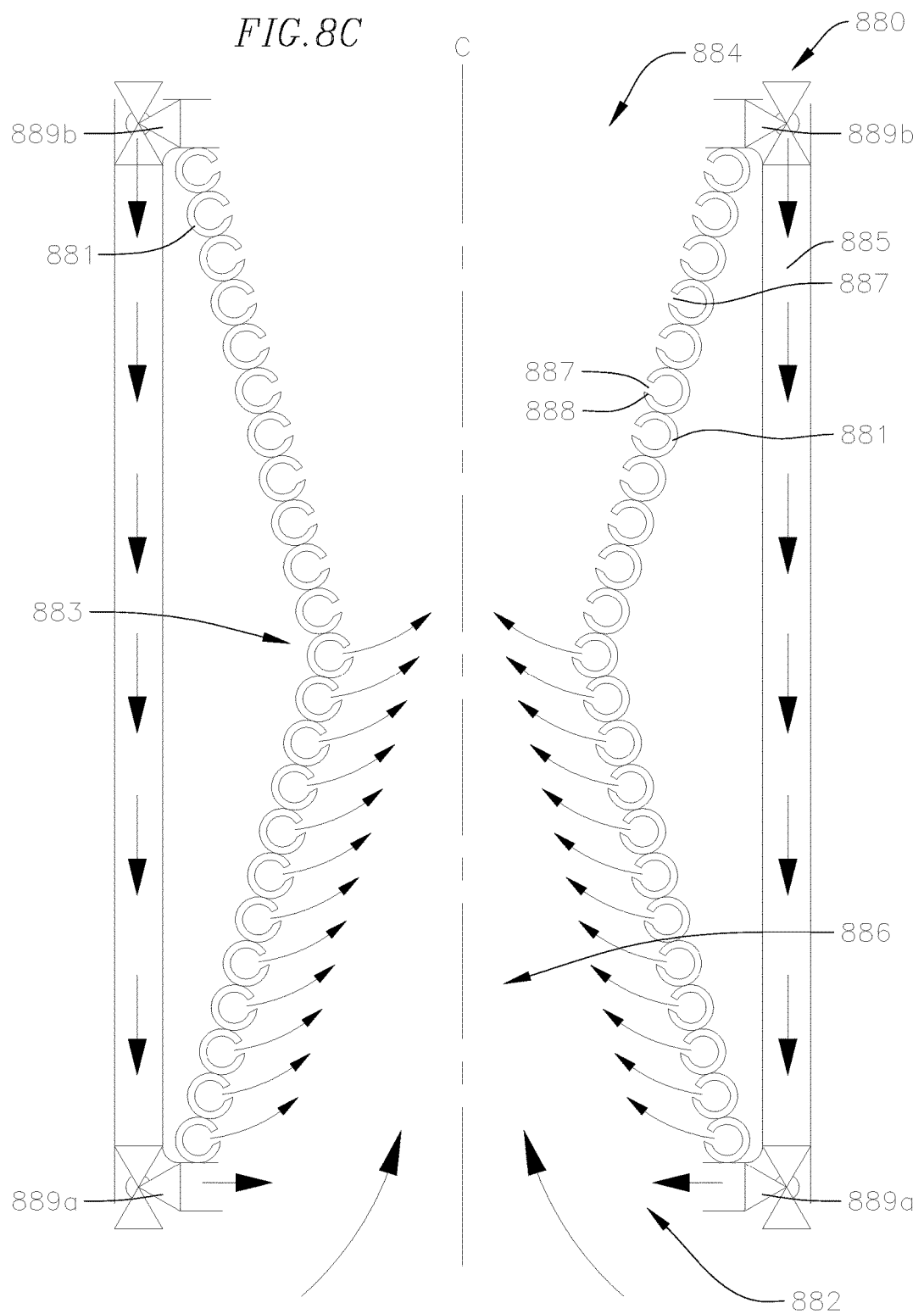

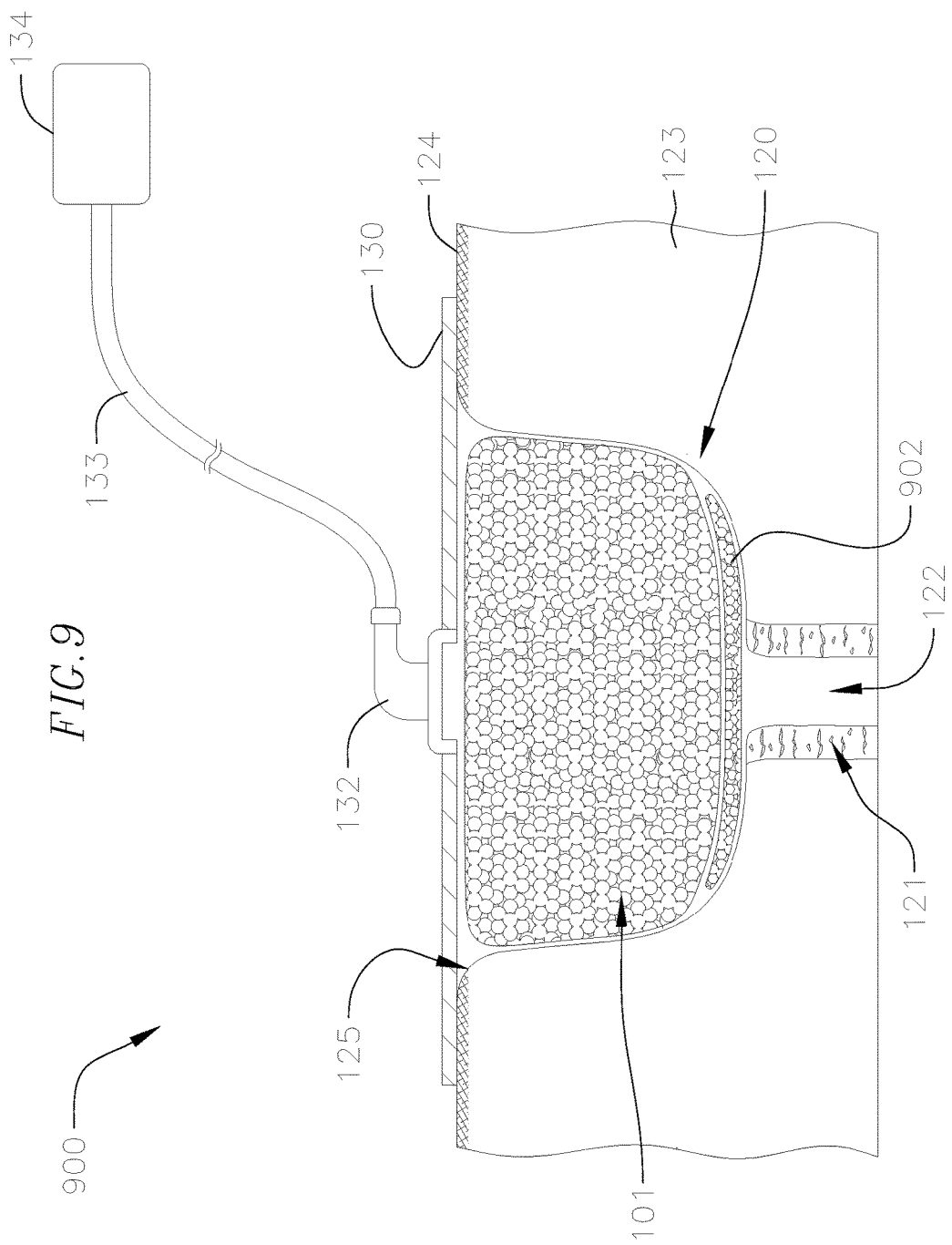

SYSTEMS AND METHODS FOR TISSUE HEALING

CROSS-REFERENCE TO RELATED APPLICATION(S)

This application is a national stage application, and claims priority to and the benefit of International Application No. PCT/US2015/015968 filed on Feb. 13, 2015, which claims the benefit of U.S. Provisional Application No. 61/940,245 filed Feb. 14, 2014, the entire contents of which are incorporated herein by reference.

BACKGROUND

Negative pressure wound therapy is a therapeutic technique used to promote healing and closure of various types of acute or chronic wounds in the human body. Negative pressure wound therapy is a wound bed management technique that creates an environment of sub-atmospheric pressure over the wound bed to draw fluid out of the wound. The effect of the sub-atmospheric pressure environment is to reduce inflammation and increase blood flow within the wound, providing a more oxygen rich environment to the wound and improve the delivery of wound-healing white blood cells, proteins, carbohydrates, and growth factors.

Generally, the wound is irrigated with saline and/or antibiotics, and may be covered with a non-adherent material that adapts to the contours of the wound. An absorptive dressing is applied over the non-adherent material and an occlusive material is applied over the dressed wound to form an air-tight seal. A vacuum tube is connected to an opening in the occlusive material. A vacuum pump applied to the vacuum tube provides the negative pressure needed to draw fluid through the wound for collection and removal. The non-adherent material and/or the absorptive dressing may be changed according to various factors such as the amount of fluid output from the wound, the patient's age, clinical objectives, and the like.

The absorptive dressing may include any one of a number of materials that are chosen as a function of the type of wound, clinical objectives, and the comfort of the patient. For example, the absorptive dressing may include cotton gauze for shallow wounds such as pressure sores or diabetic ulcers of the skin. The absorptive dressing may include a foam material for open cavity wounds such as gunshot wounds, leg ulcers, and surgically created cavities. These wounds may be lightly, moderately, or heavily exuding wounds that may benefit from the high absorption capacity of foam material. The foam material may be cut to fit the margins of the open cavity wound and placed inside the wound. Conventional foam materials generally have pore diameters in the range of approximately 100 μm-600 μm and are consistently used with a protective layer, typically petrolatum gauze, between the foam material and the wound bed in wounds involving fistulas, tendons, nerves or sensitive tissues.

SUMMARY

Various embodiments of the invention provide dressings, systems and methods for a negative pressure wound therapy system for healing a wound in a patient. Dressings, systems and methods according to various aspects of the present invention may include an ester-based material adapted to be directly applied to the wound, such as a smooth muscle fistula, without substantially damaging tissue in the wound during dressing changes. The ester-based material may have an affinity for the wound bed surface and/or wound fluid. Under pressure, the ester-based material may promote uniformity of wound fluid movement through the wound and dressing and regulate temperature within the wound.

In addition, systems and methods according to various aspects of the present invention may include a device adapted to close a wound such as a smooth muscle fistula.

BRIEF DESCRIPTION OF THE DRAWINGS

A more complete understanding of the present invention may be derived by referring to the detailed description when considered in connection with the following illustrative figures. In the following figures, like reference numbers refer to similar elements and steps throughout the figures.

Elements and steps in the figures are illustrated for simplicity and clarity and have not necessarily been rendered according to any particular sequence or scale. For example, steps that may be performed concurrently or in different order are illustrated in the figures to help to improve understanding of embodiments of the present invention. In addition, graphical representations of structural features have been simplified for the purposes of illustration.

Figure 1:
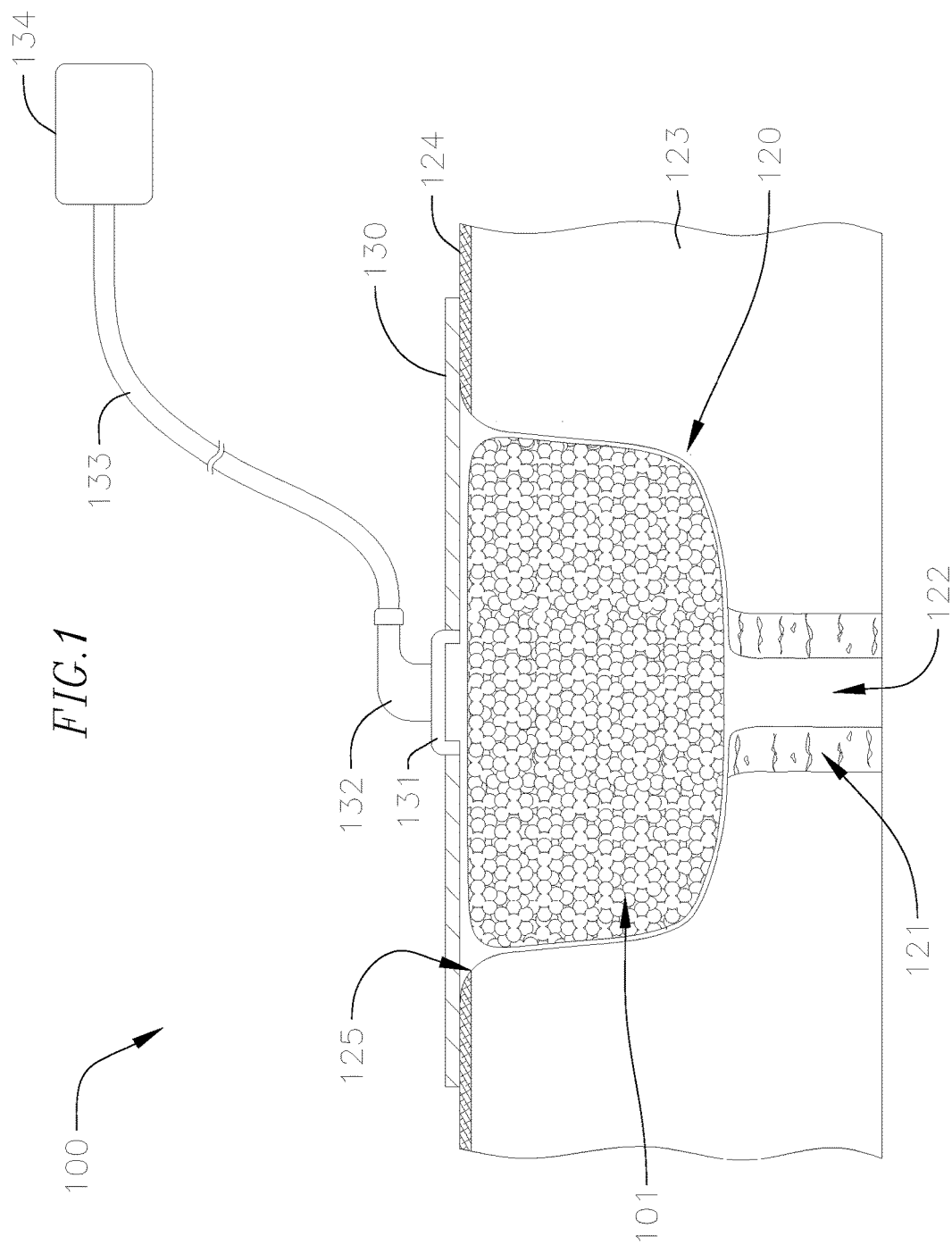
Figure 3A:
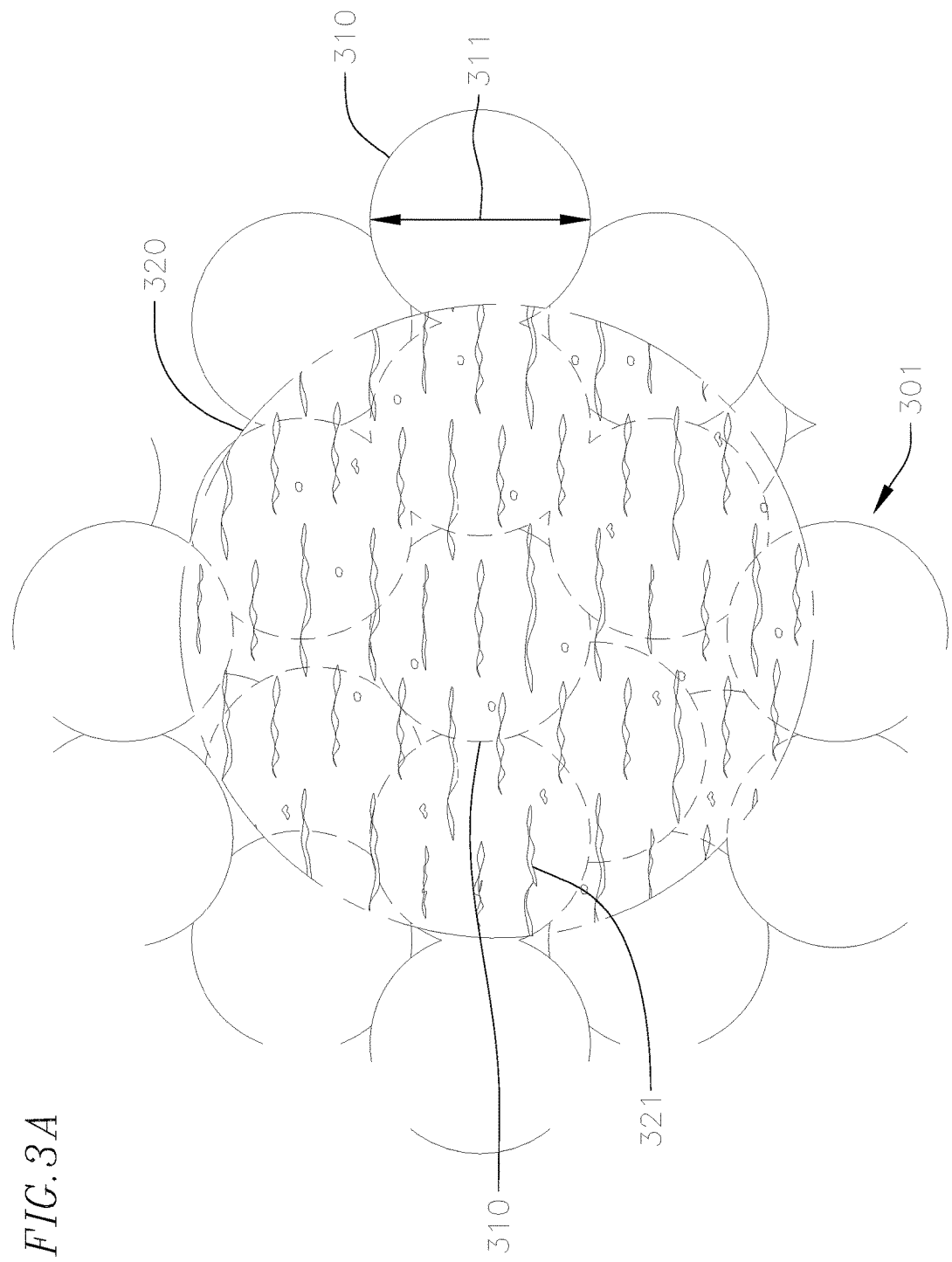
Figure 3B:
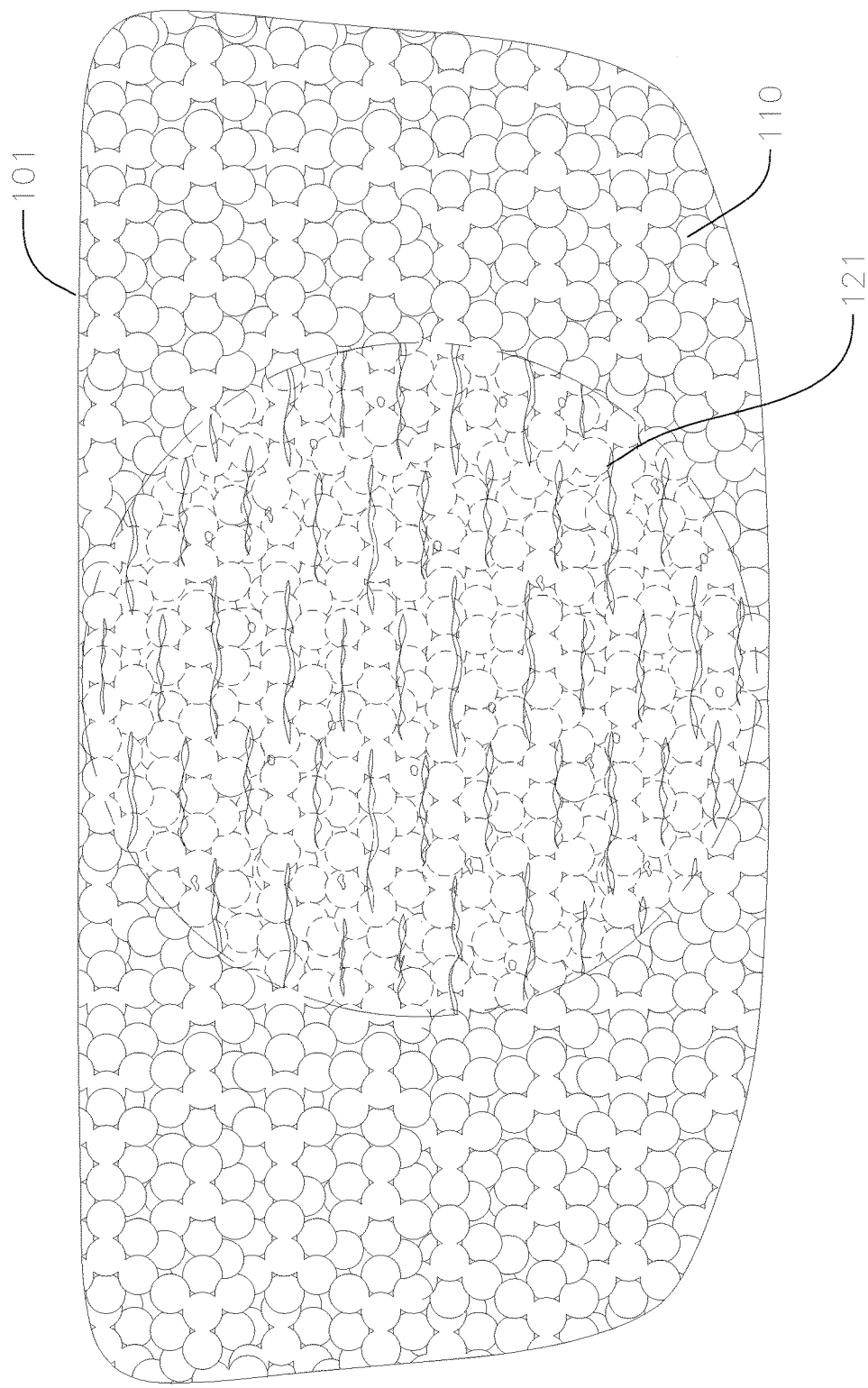
Figure 4:
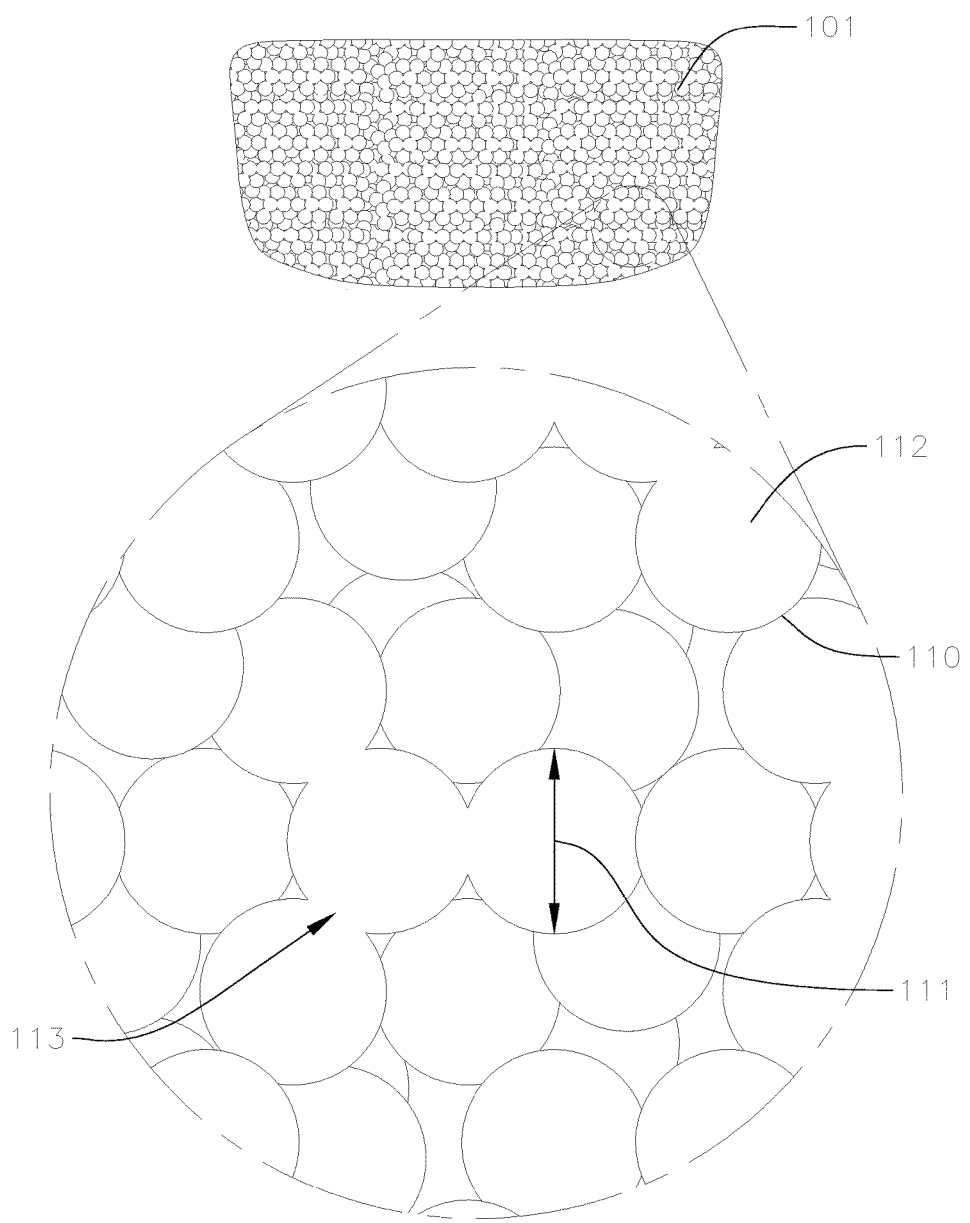
Figure 5A:
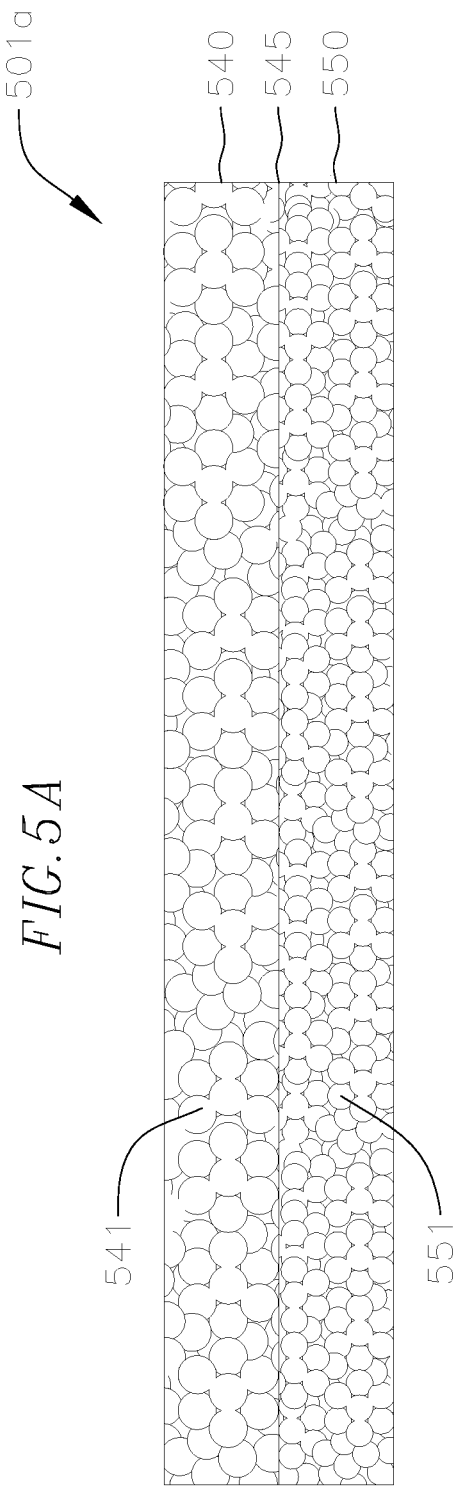
Figure 5B:
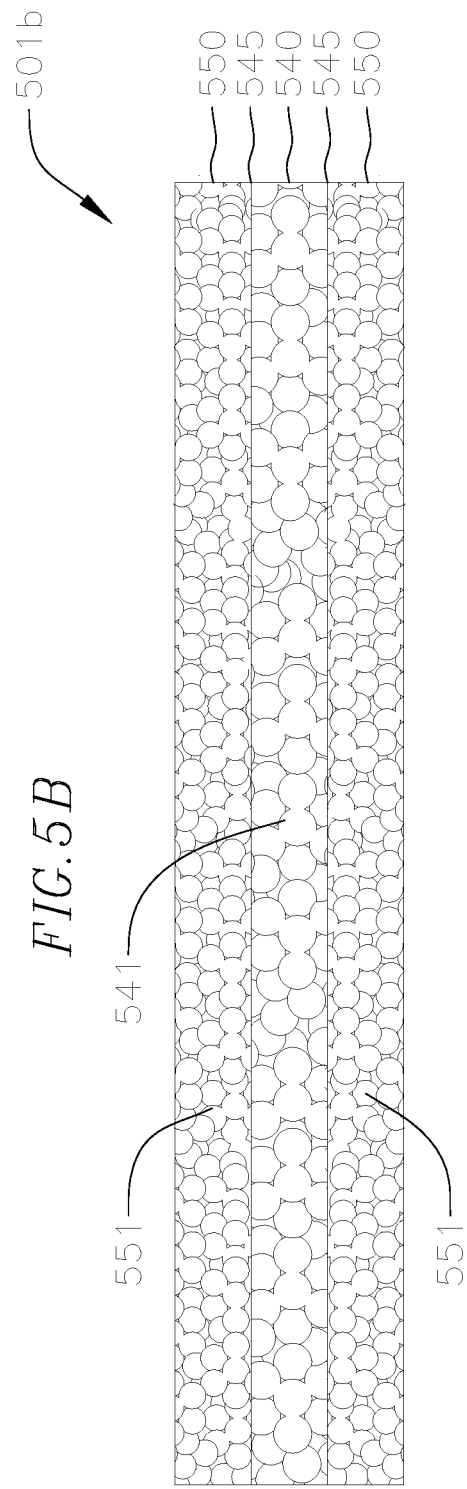
Figure 5C:
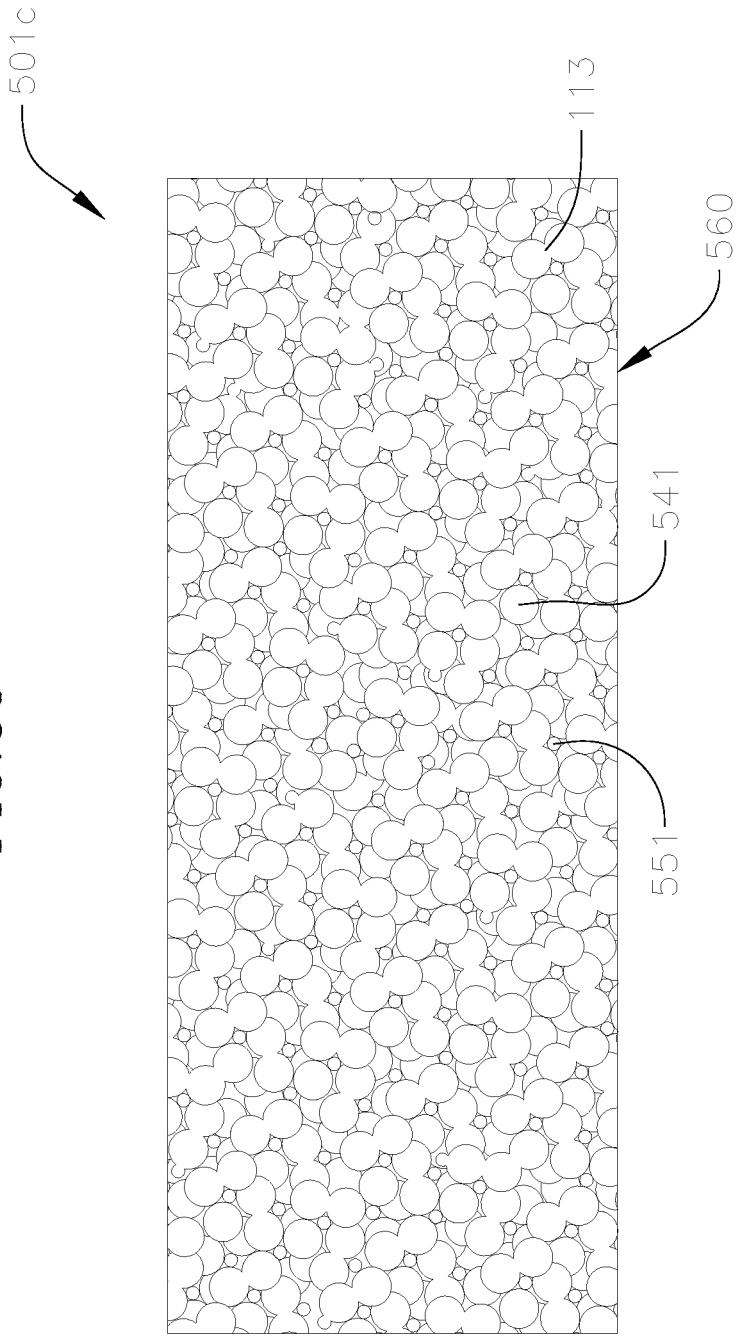
Figure 6:
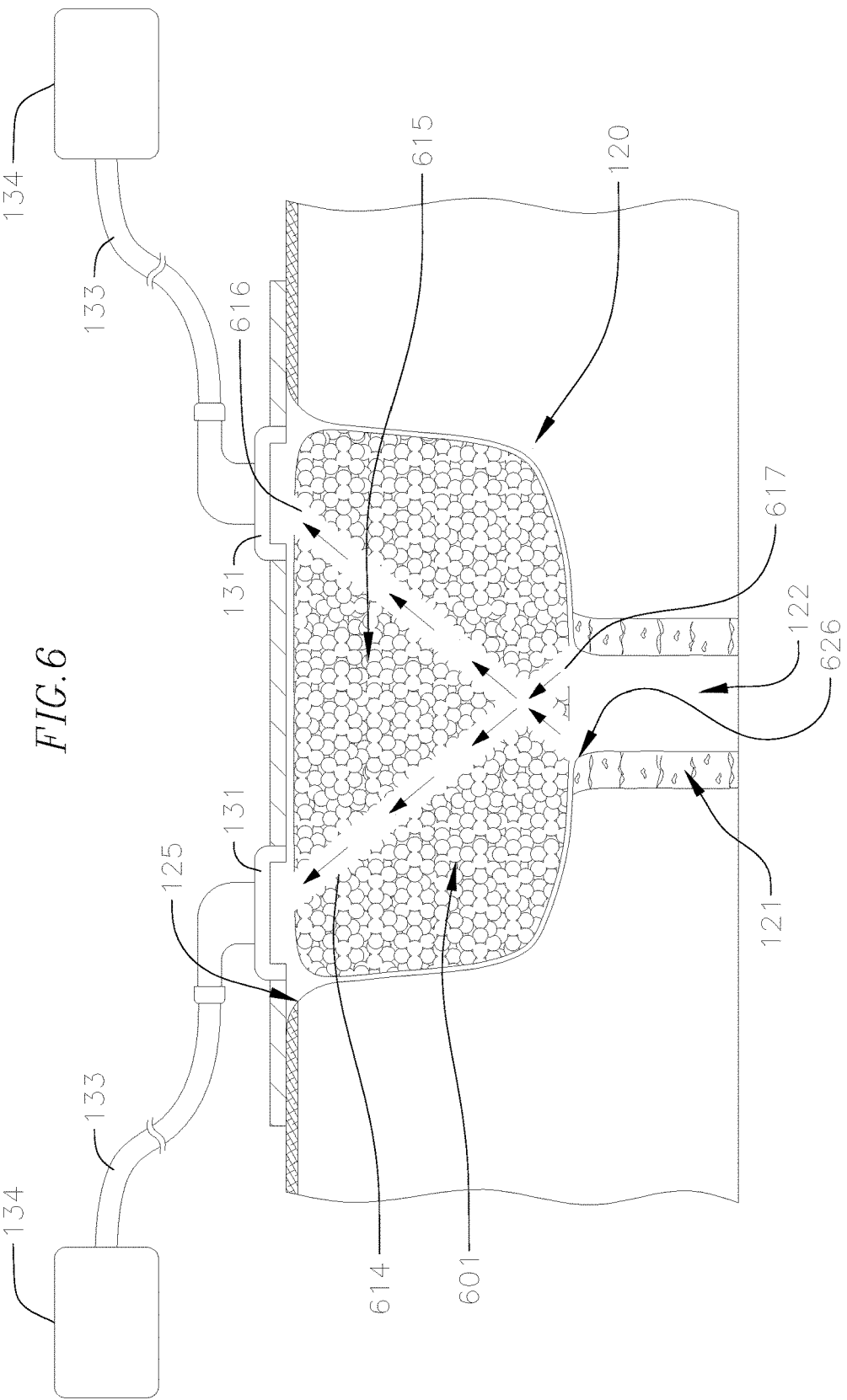
Figure 8A:
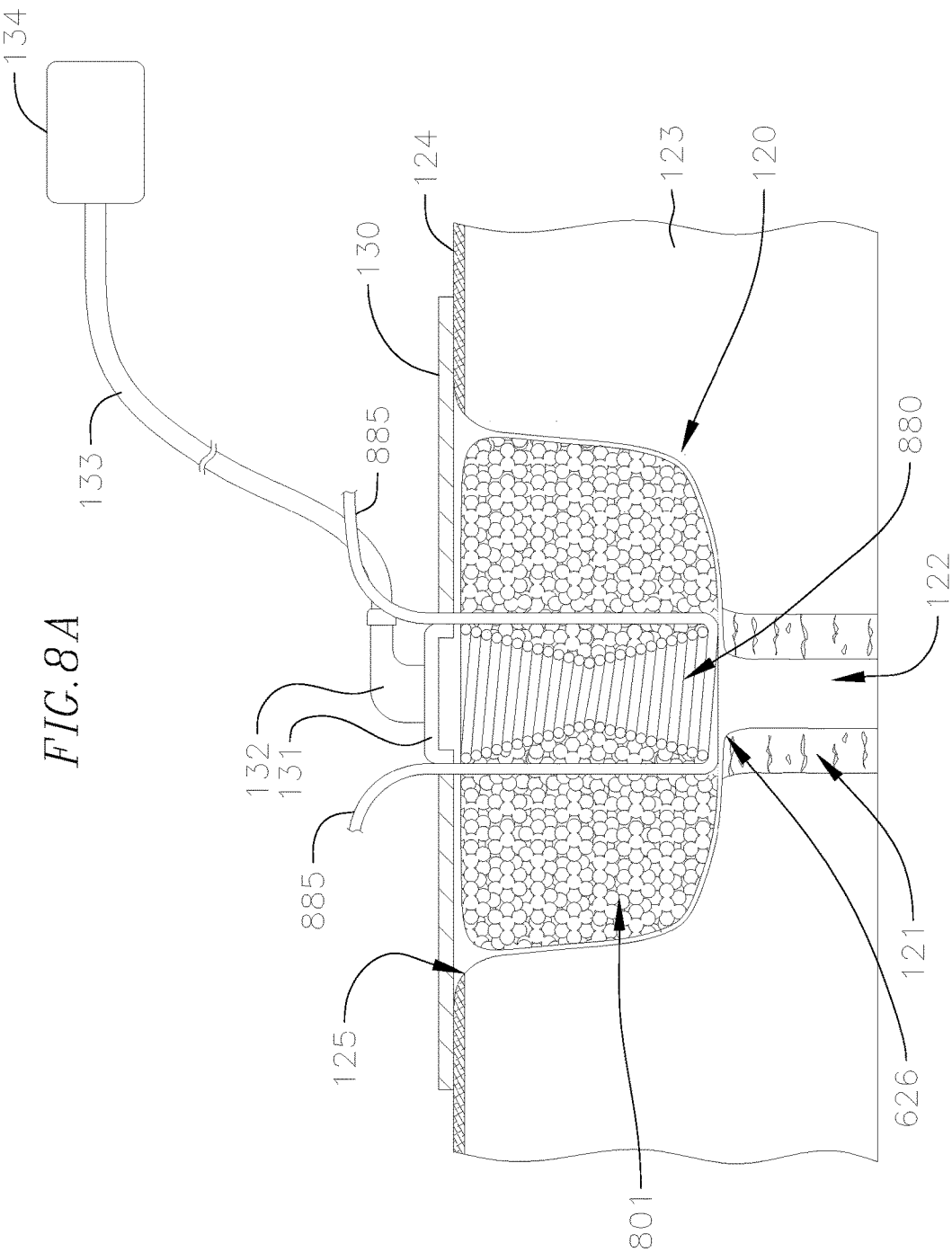
Figure 8B:
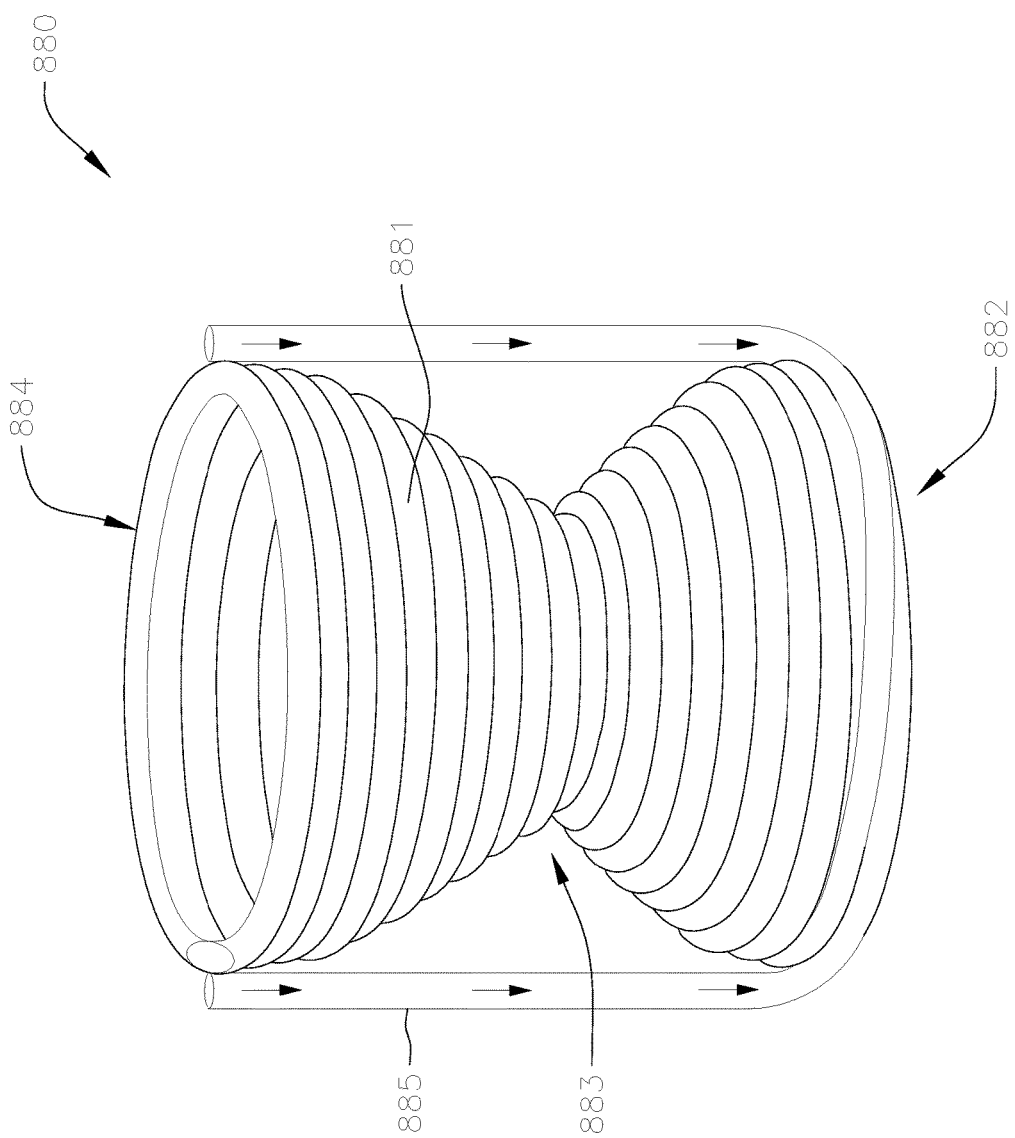
Figure 8D:
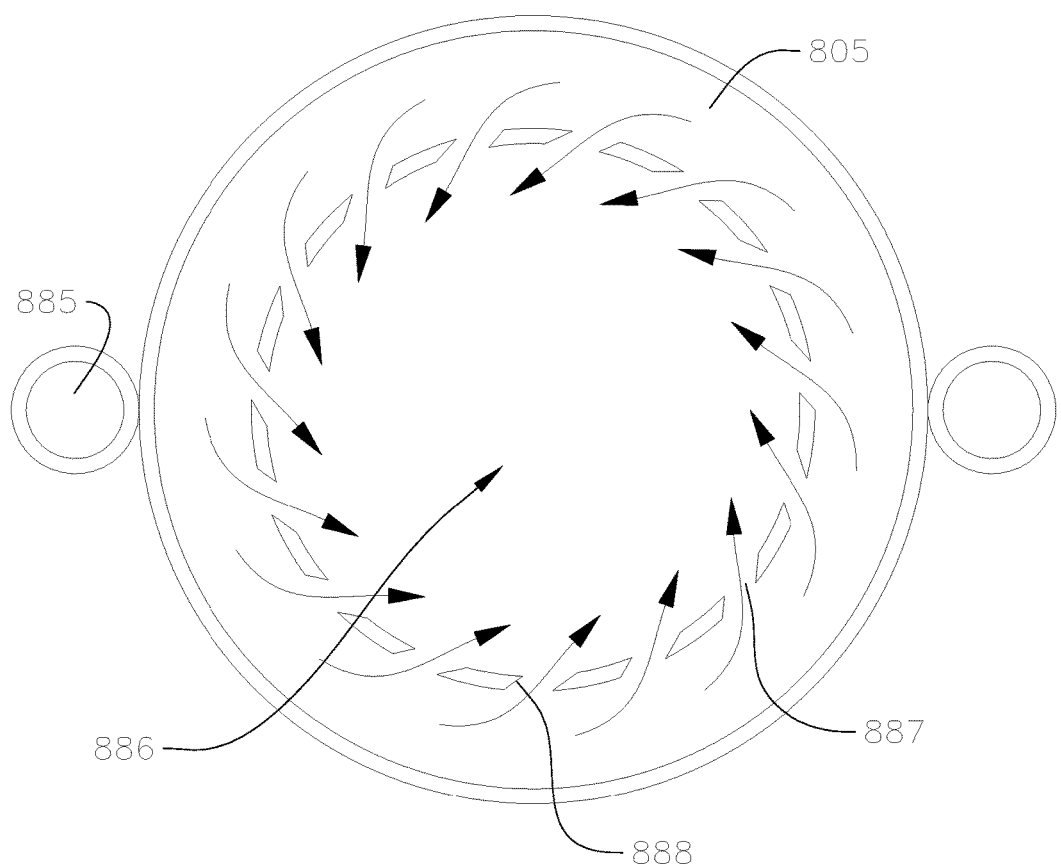

The figures described are for illustration purposes only and are not intended to limit the scope of the present disclosure in any way. Various aspects of the present invention may be more fully understood from the detailed description and the accompanying drawing figures, wherein:

FIG. 1 schematically illustrates a simplified cross-section of a negative pressure wound therapy treatment system including an absorptive dressing according to an embodiment of the present invention;

FIG. 2 schematically illustrates a simplified cross-section of a negative pressure wound therapy treatment system including an integral vacuum according to another embodiment of the present invention;

FIG. 3A schematically illustrates cell sacrifice in relation to the pore size of a conventional absorptive dressing;

FIG. 3B schematically illustrates cell sacrifice in relation to the pore size of the absorptive dressing of the embodiment of FIGS. 1 and 2;

FIG. 4 schematically illustrates a detailed pore structure of the absorptive dressing of the embodiment of FIGS. 1 and 2;

FIGS. 5A-5C schematically illustrate simplified cross-sections of absorptive dressings with various pore sizes and/or multiple layers according to further embodiments of the absorptive dressing of FIGS. 1 and 2;

FIG. 6 schematically illustrates a simplified cross-section of another embodiment of a negative pressure wound therapy treatment system including an absorptive dressing having preformed flow paths to direct wound fluid flow;

FIG. 7A schematically illustrates a simplified cross-section of a further embodiment of a negative pressure wound therapy treatment system including an absorptive dressing having barriers to direct wound fluid flow;

FIG. 7B representatively illustrates a simplified cross-section of a barrier of FIG. 7A;

FIG. 8A schematically illustrates a simplified cross-section of a further embodiment of a negative pressure wound therapy treatment system including an absorptive dressing having a radial housing to direct wound fluid flow;

FIG. 8B representatively illustrates a simplified perspective view of the radial housing of FIG. 8A;

FIG. 8C representatively illustrates a simplified cross-sectional view of the radial housing of FIG. 8B;

FIG. 8D representatively illustrates a simplified cross-sectional view of the radial housing of FIG. 8C along line I-I';

FIG. 9 schematically illustrates a simplified cross-sectional view of a negative pressure wound therapy treatment system including a healing layer that may be incorporated into the embodiments of the negative pressure wound therapy treatment system.

DETAILED DESCRIPTION

The present invention may be described in terms of functional block components and various processing steps. Such functional blocks may be realized by any number of components configured to perform the specified functions and achieve the various results. For example, the present invention may employ various process steps, apparatuses, systems, methods, etc. In addition, the present invention may be practiced in conjunction with any number of systems and methods for treating open wounds. Further, the present invention may employ any number of conventional techniques for wound treatment, wound bed preparation, treating or preventing infection of wounds, reducing inflammation, extracting fluid from wounds, changing wound dressings, and preventing the advancement of wound edges.

The particular implementations shown and described are illustrative of the invention and its best mode and are not intended to otherwise limit the scope of the present invention in any way. Indeed, for the sake of brevity, conventional manufacturing, connection, preparation, and other functional aspects of the system may not be described in detail. Furthermore, the connecting lines shown in the various figures are intended to represent examples of functional relationships and/or steps between the various elements. Many alternative or additional functional relationships or physical connections may be present in a practical system.

The terms "comprises", "comprising", "includes" or "including" or any variation thereof, are intended to reference a non-exclusive inclusion, such that a process, method, article, composition, system, or apparatus that comprises a list of elements does not include only those elements recited, but may also include other elements not expressly listed or inherent to such process, method, article, composition, system, or apparatus.

Expressions such as "at least one of," when preceding a list of elements, modify the entire list of elements and do not modify the individual elements of the list. Further, the use of "may" when describing embodiments of the present invention refers to "one or more embodiments of the present invention."

When a first element is described as being "coupled" or "connected" to a second element, the first element may be directly "coupled" or "connected" to the second element, or one or more other intervening elements may be located between the first element and the second element.

Spatially relative terms, such as "beneath", "below", "lower", "downward", "above", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

It will be understood that, although the terms "first", "second", "third", etc., may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section, without departing from the spirit and scope of the inventive concept.

The terminology used herein is for the purpose of describing particular embodiments only and is not intended to be limiting of the inventive concept. As used herein, the singular forms "a", "an" and "the" are intended to include the plural forms as well, unless the context clearly indicates otherwise.

As used herein, the term "substantially," "about," and similar terms are used as terms of approximation and not as terms of degree, and are intended to account for the inherent deviations in measured or calculated values that would be recognized by those of ordinary skill in the art.

Various representative implementations of the present invention may be applied to any area of damaged tissue on the body of a human or animal. In some embodiments, the damaged tissue may include a penetrating wound that may expose underlying tissue where wound closure is desired. In one embodiment, the present invention may be applied to incisional wounds. The penetrating wound may also include wounds caused by surgery and/or trauma, fistulas including smooth muscle fistulas, lacerations, thermal injuries such as burns, chemical wounds, electrical wounds, and the like. For example, the damaged tissue may include one or more fistulas. Fistulas may result from various traumas, including gunshot wounds, Caesarean sections, Crohn's disease, and various other diseases, injuries or surgery. Fistulas can occur between two epithelialized surfaces, such as blood vessels, skin, intestines or other hollow organs. One type of commonly occurring fistula is an enterocutaneous fistula, which occurs between the intestine and the skin surface. However, the present invention is not limited thereto, and may be applied to a various types of fistulas, including other fistulas of the digestive system or fistulas located in other systems of the body.

In some embodiments, various representative implementations of the present invention may be applied to any system for promoting healing of a wound bed including smooth muscle tissue. Certain representative implementations may include, for example, any suitable system or method for providing an at least partially or fully occlusive wound dressing for the treatment and healing of fistulas in smooth muscle tissue using negative pressure wound therapy. In one embodiment, a negative pressure wound therapy system may include an absorptive dressing applied directly in contact with the wound bed for absorbing wound fluid. In some embodiments, one or more of a healing layer may optionally be applied to a wound bed including smooth muscle tissue beneath the absorptive dressing and may further encourage wound closure and healing. The healing layer may be overlaid with the absorptive dressing for absorbing wound fluid from the wound bed. An occlusive seal may overlay the absorptive dressing and the wound edge. A vacuum pump may be coupled to a vacuum tube that may be connected to the occlusive seal with communication of the negative pressure through the absorptive dressing to the wound bed. Activation of the vacuum pump may cause withdrawal of the wound fluid from the wound bed into the absorptive dressing for removal with dressing changes.

A smooth muscle fistula may be an open cavity wound including exposed smooth muscle tissue. Unlike cardiac and skeletal muscle, which include firm and relatively coarse tissue, smooth muscle is fragile, friable, and easily damaged or stripped when touched with a foreign object. Negative pressure wound therapy using any conventional absorptive dressing such as foam or gauze are contraindicated in the treatment of certain fistulas due to the fragile nature of, for example, cardiac tissue, nerve tissue, tendon, exposed blood vessels, and smooth muscle tissue. Specifically, the clinical standard of practice does not allow direct contact of the foam or gauze or any conventional absorptive dressing to any wound including smooth muscle because such direct contact is known to cause damage to smooth muscle tissue, aggravating the wound and preventing healing. Without being bound by theory, it is believed that such systems inappropriately draw wound fluid non-uniformly from the fistula, increase the down growth of tissue into the wound, and cause undesirable cell sacrifice during dressing changes. For at least these reasons, fistulas are generally treated with mechanical attempts to close the wound by methods such as suturing, gluing, and/or stapling the fistula closed. Such mechanical wound closures have marginal success in promoting the healing of fistulas.

Referring to FIG. 1, a negative pressure treatment system 100 may include an absorptive dressing 101. In one embodiment, the absorptive dressing 101 may be placed in direct contact with a wound bed 120. The wound bed 120 may include smooth muscle tissue 121 surrounding a smooth muscle fistula 122. The absorptive dressing 101 may also contact various tissues 123 adjacent to the fistula 122 and in the wound bed 120, including skeletal and smooth muscle tissue, bone (not shown), and other tissues. An occlusive material 130 may overlay the absorptive dressing 101 and adhere to skin 124 flanking the edges 125 of the wound bed 120. The application of the occlusive material 130 may provide an airtight seal over the wound bed 120. The occlusive material 130 may include any suitable airtight material, such as plastic. In one embodiment, an adapter 131 may be coupled to the occlusive material 130 to provide an access point through the occlusive material 130 for the passage of gas or wound fluid while maintaining the airtight seal of the occlusive material 130 over the wound bed 120. A conventional vacuum tube connector 132 may be coupled to the adapter 131. A vacuum tube 133 may be coupled to the vacuum tube connector 132 and to a vacuum pump 134. The vacuum pump 134 may include any suitable conventional vacuum pump used with negative pressure therapy systems such as a piezoelectric pump, a sound wave pump, and/or a mechanical pump. Such conventional vacuum pumps may be capable of applying negative pressure in the amount of 0-200 mm Hg. Activation of the vacuum pump 134 may provide a reduced pressure environment over the wound bed 120.

In use, medical personnel, such as a doctor, may apply the absorptive dressing 101 directly to the wound bed, which includes the smooth muscle fistula 122. Wound fluid may begin to be absorbed into the absorptive dressing 101. An occlusive material 130 may be overlaid on the absorptive dressing 101 such that it fully covers the edges 125 of the wound bed 120. Medical personnel may then exert pressure on the occlusive material 130 until it adheres to the skin 124 and creates an airtight seal over the wound bed 120. The adapter 131 may be connected to a source of negative pressure, for example, a vacuum pump 134. The vacuum pump 134 may be assembled with the vacuum tube connector 132 and the vacuum tube 133 in order to connect to the adapter 131. The adapter 131 may also be connected to the access point in the occlusive material 130 to allow negative pressure to flow from the vacuum pump 134 to the absorptive dressing 101. Upon activating the vacuum pump 134, negative pressure may be applied to the absorptive dressing 101 thereby withdrawing wound fluid from the absorptive dressing 101 and the wound bed 120.

In the alternative embodiment of FIG. 2, a negative pressure treatment system 200 may include a vacuum pump 234 integrated into the absorptive dressing 101. In this embodiment, the vacuum tube 133 or vacuum tube connector 132 may not be needed. The integral vacuum pump 234 may allow a patient with the smooth muscle fistula 122 to have improved freedom of movement or allow the patient to be fully ambulatory while using the negative pressure treatment system 100. Such movement may be restricted when the vacuum tube 133 is connected to the external vacuum pump 134 as shown in FIG. 1. This embodiment functions similar to the embodiment of FIG. 1, however, medical personnel need not assemble a separate vacuum tube connector, vacuum tube or adapter in order to apply negative pressure to the absorptive dressing 101.

In various embodiments of the present invention, the absorptive dressing 101 may include any biocompatible absorptive material suitable for direct contact with wounds, such as wounds including smooth muscle. In one embodiment, the biocompatible absorptive material may have an affinity for living tissue and/or wound fluid. The wound fluid may include exudate, transudate, extracellular matrix, blood, and/or any other type of fluid coming from the wound having a variety of viscosities. In some embodiments, the biocompatible absorptive material may be capable of absorbing and/or suspending wound fluid having the variety of viscosities. In some embodiments, the biocompatible material may be adapted to contact smooth muscle 121 without causing substantial cellular disruption or damage in a reduced pressure environment and/or during dressing changes. In some embodiments, the absorptive dressing 101 may include an ester-based material.

The ester-based material may be formed into a foam suitable for trimming to fit the boundaries of the wound bed 120, such as fitting to the edges 125. The ester-based material may include ester functional groups that may be exposed to and/or directly contact the surface of the smooth muscle 121. The ester functional group is a carboxylic acid derivative having the general chemical formula

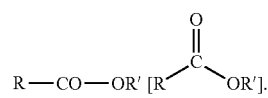

Esters may be derived from an inorganic acid or organic acid in which at least one —OH (hydroxyl) group is replaced by an —O-alkyl (alkoxy) group. The carbonyl oxygen of the ester functional group may have a partial negative charge with a delocalized carbocation. The ester functional group may be capable of at least three chemical reactions. First, the electrophilic carbocation may be vulnerable to nucleophilic attack by another molecule, such as hydroxide, resulting in addition of the nucleophile to the carbocation. Such nucleophilic attack may result in hydrolysis of the ester. Second, an electrophile may be accepted by the highly electronegative carbonyl oxygen. The electrophile may be a hydrogen ion. Accordingly, the carbonyl oxygen may participate in intermolecular hydrogen bonding. Third, the carbon adjacent to the carbocation may undergo deprotonation by a base and leave a negative charge on the adjacent carbon or the carbonyl oxygen, as stabilized by resonance structures.

In various embodiments, any one or more of these ester functional group reactivities may participate in the affinity of the ester-based material for living tissue and/or the wound fluid, in particular when applied directly to the smooth muscle tissue 121. The ester functional group may have an affinity for a variety of molecules in the wound bed 120, including polar groups on cells in the wound bed 120 such as the phospholipid bilayer of cell membranes, the water component of wound fluid produced by the wound bed 120, and the water component of fluid coming through the smooth muscle fistula 122, such as intestinal fluid.

As described above, the ester functional groups may interact with the smooth muscle tissue 121 through hydrogen bonding, nucleophilic addition, including hydrolysis, and/or base deprotonation. Without being bound by theory, it is believed that these chemical interactions may form along the interface between the absorptive dressing 101 and the smooth muscle tissue 121, evenly spreading a lifting force of negative pressure over the exposed surface of the smooth muscle tissue 121, creating a consistent and uniform pull upward.

At least one or more of the presence of the chemical interaction of the tissue in the wound bed 120 with the ester functional groups of the absorptive dressing 101 and/or the interface layer 902 (discussed with respect to FIGS. 8A-8B below) and negative pressure from the vacuum pump may promote a uniform upward and/or inward pull of the wound bed 120. As a result of this uniform pull upward and/or inward, the ester-based material may produce little to no detrimental changes or damage to the geometric environment of the wound bed 120, may promote the uniform movement of wound fluid through the wound bed 120, and may reduce the flow of wound fluid out of the wound bed 120. The reduction of fluid and/or the pull of tissue inward may lead to closure and healing of the wound bed 120.

The reactivity of the ester functional group with the smooth muscle tissue 122 in combination with the negative pressure environment provided by the vacuum pump 134 may have a variety of effects on the wound bed 120. Without being bound by theory, it is believed that the ester functional group may promote at least one or more of: an optimal geometric environment of the wound, the formation of granulation tissue, temperature regulation, at least partial reversal of tissue downgrowth, optimal fluid management, and induction of cell growth.

The geometric environment of the wound bed 120 impacts certain physiological phenomenon including the migration of cells, such as epithelial cell growth and capillary endothelial cell migration, and the movement of exudate through the wound carrying growth factors, nutrients, and proteins. As discussed further below, without being bound by theory, non-uniform movement of wound fluid can lead to the pooling of wound fluid at the wound bed. This pooling may disrupt cell-to-cell interactions and may lead to cell distortion or damage. It is believed that the ester-based material limits such cellular distortions and maintains an optimal or improved geometric environment for wound healing and closure. This may be due to the chemical interactions of the ester functional groups with the tissue of the wound bed 120.

Granulation tissue may include new connective tissue and the formation of new blood vessels on the surface of the wound bed 120, facilitating the healing process. The growth of granulation tissue may fill the wound bed 120 and assist in closure of the wound and/or the reduction of exudate output. The application of the ester-based material to the wound bed 120 including the smooth muscle fistula 122 may stimulate tissue granulation.

Maintaining a normal temperature in the wound bed 120 may prevent vasoconstriction and hypoxia and may decrease the risk of infection. The small pore diameter 111 of the ester-based material which provides an even distribution and movement of the exudate throughout the absorptive dressing 101 may effectively regulate the normal temperature of the wound bed 120 by reducing evaporation and/or uneven airflow through the ester-based material. Evaporation and/or uneven airflow, such as that exhibited by ether-based materials, may cause the wound temperature to drop which may increase tissue metabolism and decrease pH. These changes in the wound tissue metabolism and pH may cause bleeding, disruption of granulation tissue formation, and pain for the patient.

The absorptive dressing 101 including the ester-based material in combination with continuous or intermittent negative pressure may provide enhanced temperature regulation of the wound bed 120. In various embodiments of the present invention, the ester-based material may provide temperature regulation in one or more locations on the ester-based material. First, the interface between the surface of the ester-based material and the tissue of the wound bed 120 where the ester functional groups make direct contact and react with the tissue may consistently maintain a substantially normal body temperature. Second, the remaining portion of the ester-based material may evenly distribute and interact with the exudate pulled from the wound bed 120, forming chemical bonds such as hydrogen bonds with the exudate as the exudate moves through the ester-based material towards the source of negative pressure. The exudate in the ester-based material may establish a temperature equilibrium which may be lower than body temperature and may provide a layer of insulation over the ester-based material to tissue interface. As described above, effective regulation of the temperature of the wound bed may positively affect healing providing an optimal temperature for cellular metabolism and pH maintenance. Additionally, the ester-based material may provide a thermal buffer to increase the temperature of incoming instillation fluids such as saline that may be applied to the negative pressure treatment system 100, such as for the addition of antibiotics to the wound, and may prevent or reduce a low temperature shock to the wound bed 120.

The chemical interactions of the ester functional groups in the ester-based material with the tissue of the wound bed 120 may result in improved fluid management as compared to non-ester based materials. The evenly distributed affinity of the ester functional groups for the tissue and exudate may allow exudate to move through the wound in an even and orderly manner toward the source of negative pressure, despite the effect of microstrain distortions of the surface of the wound bed 120 in response to the negative pressure. This affinity may promote consistent collection of exudate fluid in folds and contouring lines of the wound bed 120. The effect of the uniform movement of exudate provides efficient removal of exudate, fluids, and materials and promotes the uniform orientation of cell growth throughout the surface of the wound bed 120. Without being bound by theory, the uniform affinity of the ester functional groups may also prevent or decrease the formation of cavities or undermined tissues due to the closer connection between the tissue and the ester-based material. Further, the uniform affinity of the ester functional group for the tissue may require less cellular work to orient and re-orient during physical movements of the patient and changes in the negative pressure treatment system 100. Thus, systems used in the industry, such as the instillation of external fluids, soak, vacuum pause cycles, and/or dressing changes, to abate issues of fluid pooling may not be as necessary or may lead to even further improved results when used with the ester-based material.

An upward pull induced by the interaction of the ester functional groups with the tissue on the surface of the wound bed 120 may reduce and/or at least partially reverse naturally occurring tissue down growth into the wound bed 120. Down growth of epithelial tissue and deeper tissue into the wound bed 120 may occur naturally in incisions and wounds. However, an upward pull provided by the ester-based material on the wound bed 120 may uniformly distribute pressure over the surface of the wound bed 120 and cause migrating cells to move toward the surface of the wound bed 120.

In one embodiment, the ester-based material may be a polymer of polyurethane, specifically polyester. As compared to conventional ether-based foams, ester-based foams are more rigid, have a smaller open-reticulated cell structure, and have a higher tensile strength. Ester-based foams also suspend moisture substantially evenly and allow fluid to flow evenly throughout the foam due to its small cell structure and/or chemical affinity for moisture.

Conventional foams are typically ether-based foams, including polymers of polyether triol, and have a larger pore diameter. Without being bound by theory, it is believed that these relatively large pore sizes, as compared to the sizes of individual cells with which the foam material was used, such as smooth muscle cells, are responsible for the damage caused to wound beds when conventional foam material is placed in direct contact with the wound. FIG. 3A representatively illustrates an example of pore diameters 311 of conventional foam materials 301 compared to smooth muscle cells 321.

In addition, without being bound by theory, it is believed that the large pore diameter of ether-based foams reduces the foam's ability to suspend moisture and allow moisture to pass through the foam easily. The ease of movement of moisture through the ether-based foam has the practical result of promoting fluid collection in the portion of the foam having the lowest center of gravity, leading to an uneven distribution of moisture throughout the ether-based foam. The poor ability of ether-based foams to retain moisture renders them inappropriate for use in negative pressure therapy applications because the ether-based foam provides inadequate temperature regulation to the wound bed, poor delivery of additives to the wound bed such as antibiotics, and limits ambulation of a patient due to the uneven distribution and pooling of moisture in a sealed system when the patient moves.

Additionally, the basic chemical structure of the ether linkage in ether-based polyurethane foams is R—O—R'. The central oxygen may be substantially unreactive, incapable of appreciable hydrogen bonding, and significantly less polar than the oxygen of ester functional groups. Without being bound by theory, it is believed that the stability of the ether linkage renders them incapable of forming the same types of chemical interactions or reactions as ester-based foams including hydrolysis and reactions with acids, oxidizing agents, reducing agents, bases, and active metal species. The chemical and resultant structural differences between ether-based foams and ester-based foams impact the performance of these materials in different applications. In healing applications using negative pressure therapy systems, the temperature regulation and even distribution of moisture provided by the various embodiments of the ester-based material described may optimize wound healing and closure.

The absorptive dressing 101 including the ester-based material may be manufactured and/or further processed to obtain any desired physical properties. In some embodiments, the desired physical properties may optimize pore size and structure such as pore density, pore geometry, pore reticulation, permeability of pores to wound fluid, dry tensile strength, and/or wet tensile strength. Processing of the ester-based material may further optimize the ability of the ester-based material to maintain a saturated volume of suspended fluid. For example, the ester-based material of the absorptive dressing 101 applied to the wound bed 120 may ultimately become saturated with wound fluid coming through the smooth muscle fistula 122. Wound fluid may be continually removed from the absorptive dressing 101 through the vacuum tube 133 and, at the same time, wound fluid may continually be entering the absorptive dressing 101 from the smooth muscle fistula 122. As a result of the ester-based material's affinity for the wound fluid, a saturated absorptive dressing 101 may allow a substantially equal volume of wound fluid and/or number of wound fluid molecules into the ester-based material as is exiting the ester-based material through the vacuum tube 133. Accordingly, wound fluid removal may not substantially affect the saturated volume of wound fluid retained by the absorptive dressing 101 under clinically relevant negative pressures of 0-200 mm Hg. Without being bound by theory, it is believed that this environment where the volume in is substantially equal to the volume out (referred to simply at times as a "one molecule in/one molecule out" environment) as provided by a substantially saturated absorptive dressing 101 promotes a plurality of benefits to wound healing such as effective temperature regulation, even distribution of negative pressure, and maintaining an even distribution of wound fluid despite movement of the patient.

In other applications, the geometry of the pores of the absorptive dressing 101 may include a shape that provides for increased surface area inside the pores 110, such as a round shape. Such increased surface area may increase contact of the ester functional groups with the wound bed 120 and may benefit the healing of the smooth muscle fistula 122. The increased surface area may be particularly beneficial for a wound with a high wound fluid flow, such as an intestinal fistula. In other embodiments, the geometry of the pores 110 of the absorptive dressing 101, shown in FIG. 3B, may be configured to correlate with the general shape of the primary cell type in the wound bed 120, such as epithelial cells, skeletal muscle cells, and/or smooth muscle cells. In addition, the pores may be configured to correlate with the size and/or diameter of any of the cells or other material of the exudate from the wound bed. For example, the pores 110 may have an elongated shape to correlate with the elongated dimensions of skeletal or smooth muscle cells. Example dimensions and shapes of cell types that may be in the wound bed are shown in Table 1 below. The pores 110 may be configured to correlate with the diameter, shape and/or length of any of the cells types below, in addition to the diameter, shape and/or length of other cell types in the wound bed 120. However, the pores 110 may have a variety of shapes, including octagonal, hexagonal, diamond or trigonal.

TABLE 1

| Cell Type | General Cell Shape | Diameter | Length |
|---|---|---|---|
| MUSCLE CELLS | varies | varies | varies |
| Cardiac Muscle Cells | Short, narrow cell | 10 μm-15 μm | 80 μm-100 μm |
| Smooth Muscle Cells | Short, elongate, fusiform cell | 0.2 μm-2 μm | 20 μm-200 μm |
| Skeletal Muscle Cells | Large, elongate cell | 10 μm-100 μm | Up to 100 cm |
| EPITHELIAL CELLS (including endothelial cells) | varies | varies | varies |
| CONNECTIVE TISSUES | varies | varies | varies |
| NERVE CELLS | varies | varies | varies |

In some applications, the pore diameter and/or size of the absorptive dressing 101 may be customized to promote the interaction of the pore struts with the cells in the wound bed 120. For example, the pore diameter and/or size may be substantially equivalent to the diameter and/or size of a primary cell type in the wound bed 120. In some embodiments, the pore width may be about 0.1 μm to about 100 μm, in order to correlate with the size of smooth muscle cells. In other embodiments, the pore width may be about 0.1 μm to about 50 μm.

Without being bound by theory, it is believed that reducing the size of the pores 110 to be substantially equivalent to the diameter of smooth muscle cells leads to a reduction in cell sacrifice, as representatively illustrated in FIGS. 3A-3B. An example of pore 310s of a conventional ether-based foam 301 is illustrated in FIG. 3A. Pores 310 may have a diameter 311 of about 400 μm to about 600 μm. In general, smooth muscles cells 321 adjacent to pores 310, shown in the illustration of a portion of a wound bed 320, may be removed (e.g., sacrificed) during dressing changes. Without being bound by theory, it is believed that the sacrifice of cells 321 may be caused by the formation of weak cell-to-cell contacts, such as cell junctions, that form as damaged tissue regrows to fill a wound bed 120. The struts or edges of pores 310 in conventional ether-based foams may contact some smooth muscle cells 321 and destroy weak cell junctions formed as the smooth muscle cells 321 divide as part of wound healing. Pore 110 of the ester-based foam of an embodiment of the present invention may be illustrated in FIG. 3B. In some embodiments, pore 110 may have a diameter of about 30 μm or less and be close to the diameter of a smooth muscle cell. As a result, the pores 110 may make many contacts along the length of each smooth muscle cell 121. In this fashion, it is believed that the pores 110 may function as a scaffold to support closer and/or stronger cell junctions as the smooth muscles cells 121 divide. The smooth muscle cells 121 may therefore remain intact during dressing changes, with no appreciable loss of the smooth muscle cells 121 at the foam-tissue interface that may disrupt wound healing.

Referring to FIG. 4, in various embodiments of the present invention, the size of the pores 110 in the absorptive dressing 101 including the ester-based material may be adapted to reduce the sacrifice of the smooth muscle tissue 121. In one embodiment, the size of pores 110 may be reduced to any pore size that is less than the pore size of conventional ester-based foam of approximately 100 μm-600 μm. In some embodiments, the pore diameter 111 may be substantially equivalent to the diameter of smooth muscle cells. Smooth muscle cells include short, elongate, and fusiform shapes that may be about 0.2 μm-20 μm in diameter and approximately 20 μm-200 μm in length. In one embodiment, the average pore diameter 111 may be approximately less than or equal to 30 μm. For example, the average pore diameter 111 may be about 0.2-30 μm, or 0.2-2 μm.

Further, the pores 110 of the ester-based material may be reticulated pores. Reticulation refers to the open nature of the pores 110 such that the lumen 112 of the pores 110 communicates with adjacent pores 110, such as through channels 113. The struts or edges of the pores 110 where contact is made with adjacent pores 110 remain intact in reticulated foam. Without being bound by theory, the open-celled and substantially uniform pore size of the reticulated absorptive dressing 101 may facilitate substantially uniform diffusion of nutrients, oxygen, bioactives, and allow for negative pressure across the entire wound bed 120, and efficient removal of exudates upon application of negative pressure wound therapy.

In various embodiments of the present invention, the size of the pores 110 of the absorptive dressing 101 including an ester-based material may be less than the pore size of conventional ester foams and/or substantially similar to the diameter of smooth muscle cells 121. In one embodiment, the pores 110 may be created in an ester-based material using any suitable process such as using molds including fiber-optic molds, stamping methods, bombardment methods such as ion beam or ultrasound bombardment, chemical etching, chemical baths, and/or laser irradiation of the ester-based material.

In one embodiment, the pores of conventional ester foam may be reduced to a desired size in any suitable process such as felting. The felting process may include thermal, mechanical, or chemical compression of the ester-based material, resulting in permanently compressing the pores 110. The felting process may include heating the ester-based material during the manufacturing process of the polyurethane ester foam, followed by the application of a degree of compression to produce a desired pore density, a desired fluid dynamic within the foam, and/or an increase in tensile strength. In various embodiments, the biocompatible foam may be processed to obtain any desired physical properties such as any desired pore size, porosity, density, reticulation of pores, permeability and/or tensile strength.

In various embodiments, the ester-based material may be manufactured and/or further processed to obtain any desired chemical properties such as affinity for wound fluid, elasticity of the ester-based material to allow contraction of the absorptive dressing 101 under negative pressure, even wound fluid suspension and/or absorption within the ester-based material, and/or retention and/or delivery of additives. In some embodiments, the ester-based material may be customized to promote healing of a particular type of wound bed 120. For example, a wound bed 120 including the smooth muscle fistula 122 of a highly acidic nature, such as a biliary fistula, may benefit from an absorptive dressing 101 with an altered chemistry such as impregnation with a neutralizing composition such as bicarbonate. In another embodiment, the ester-based material may include alcohols, antibiotics, pharmaceutically active compounds, and the like. Accordingly, the chemistry, pore size, and/or the pore geometry within the absorptive dressing 101 may be optimized and/or customized to provide a maximum healing benefit to any particular type of wound bed 120. Additionally, in some embodiments, the ester-based material may include a plurality of horizontally arranged layers with the desired physical properties that are coupled to form a single cohesive piece of foam.

In further embodiments, as illustrated in FIGS. 5A-5B, the absorptive dressing may include more than one layer of foam where each layer includes a substantially uniform pore size and/or pore geometry within each layer, but has a different pore size and/or pore geometry relative to an adjacent layer or layers. For example, referring to FIG. 5A, an absorptive dressing 501a may have a first layer 540 including pores 541 having a diameter that may be larger than the pores 551 of a second layer 550. Referring to FIG. 5B, an absorptive dressing 501b may include the second layer 550 overlaid with the first layer 540 and the first layer 540 may be overlaid by an additional second layer 550. The absorptive dressing 501b may include as many alternating layers 540/550 as desired. In various embodiments, the pores 541 and 551 may be approximately the size and/or diameter of the cells with which the absorptive dressing 501a, 501b will be used. For example, the pores 551 may be about 0.1 μm to about 10 μm and the pores 541 may be about 10 μm to about 100 μm, or about 20 μm to about 100 μm. Accordingly, many pores 541 and/or pores 551 may extend the length of any smooth muscle cells in the wound bed 120. However, the pores 541 and 551 may also have any of the characteristics of the pores 110 discussed above, including any of a variety of shapes, sizes, diameters or reticulation as discussed above.

Without being bound by theory, it is believed that having such alternative layers of 540 and 550 will create a better seal via the smaller pores 551 at the wound bed 120 while still allowing for higher levels of absorption and compressibility (to compensate for peristalsis and other movements by the patient) at the larger pores 541. In addition, in the absorptive dressing 501b, having the second layer 551 on both the top and bottom of first layer 540 allows the absorptive dressing 501b to be reversible, facilitating its use by medical personnel. In such an embodiment, the pores 551 may be about 0.1 μm to about 50 μm and the pores 541 may be about 10 μm to about 300 μm. In some embodiments, the first layer 540 may have a thickness of about 0.1 mm to about 2 mm and the second layer 550 may have a thickness between 2 mm and 8 mm.

Referring to FIG. 5C, describing another embodiment of the absorptive dressing, in an absorptive dressing 501c, the pores 541 and the pores 551 may be combined within the same layer, such as a layer 560. For example, smaller pores 551 may be interspersed between larger pores 541 where each pore 551 is surrounded by larger pores 541. Additionally, the absorptive dressing 501c may include pores having a limited reticulation to reduce the volume and/or rate of wound fluid flow through the absorptive dressing 501c. The pores of layer 501c may also have any of the characteristics of the pores 110 discussed above, including any of a variety of shapes, sizes, diameters or reticulation as discussed above. For example, the pores of layer 560 may have a size of about 0.1 μm to about 300 μm.

Without being bound by theory, by interspersing different sized pores, it is believed that the wound fluid would travel through pathways including large pores 541 and smaller pores 551, increasing the resistance to fluid flow. In some embodiments, the interspersion of small pores 551 with large pores 541 may increase the resistance of the absorptive layer 501c to wound fluid, creating a tighter seal over the wound bed 120 as compared to an absorptive layer having a uniform or larger pore 541 structure. This tight seal or layer of pressure resistance may lead to lower wound fluid production and output from the wound bed 120 and/or increased wound fluid flow back through the source of the fistula, such as an intestine. Additionally, without being bound by theory, it is believed that selection of the size of small pores 551 and/or large pores 541 may provide a filtration function to facilitate removal of pre-selected particles from the wound fluid while encouraging lower wound fluid production and/or redirection of flow. For example, the size of small pores 551 and/or large pores 541 may be similar to the size of various cell debris and/or bacteria, which are generally substantially smaller than eukaryotic cells.

Layer 560 may include the entire absorptive dressing 501c, or may be layered with additional layers having interspersed large and small pores or may be layered with additional layers of uniform pores, such as first and second layers 501a and 501b. In further embodiments, any of absorptive dressings 501a, 501b and 501c may be layered with a foam having a larger pore size, such as conventional foams having a pore size between 100 μm-600 μm. In addition, any of absorptive dressings 501a, 501b and 501c may have the physical and chemical properties of the various embodiments of absorptive dressings discussed herein, for example, the absorptive dressing 101.

In various embodiments, the absorptive dressing including horizontally stacked layers, such as the layers 540, 550 and 560, may include a junction 545 between two adjacent layers, as shown in FIG. 5A. The junction 545 may be treated with any suitable additive to provide or improve a desired physical and/or chemical property of the absorptive layer 501a, 501b, 501c. For example, a solution including one or more additives may be painted, sprayed, wiped, sponged, or otherwise applied to the junction 545. The additives may include biocompatible material such as an antibacterial agent, a pharmaceutically active agent, a vitamin, a semi-occlusive substance, an emollient, a humectant, medicament, and the like. The absorptive dressing 501a, 501b, 501c may be soaked and/or saturated in the additive prior to or upon its application onto the wound bed 120.

The method or use for the absorptive dressings 501a, 501b and 501c is the same as the method of use for the embodiment of FIG. 1. However, in embodiments in which the absorptive dressings 501a, 501b and 501c are not reversible, i.e., in which the outermost layers of the absorptive dressings 501a, 501b and 501c have different pore sizes, the outermost layer with the smallest pore size may face the wound bed in order to create a tighter seal over the wound bed 120.

In further embodiments, additional structural features (which may also be referred to as secondary structural features whereas the pores of the absorptive dressing may be referred to as primary structural features) may be introduced into the absorptive dressing to encourage wound closure by directional wound fluid flow through the absorptive dressing. Such structural features may direct wound fluid flowing from the edges 125 of the wound bed 120, particularly the edges 626 of the fistula 122, toward a central area above the fistula 122 to promote a pull of the tissues toward a midline of the fistula 122. Conventional absorptive dressings, such as ether-based foams, do not discretely or intentionally employ structural features that influence or guide the direction of wound fluid through the absorptive dressing. Any suitable method for creating directional fluid flow may be implemented within the absorptive dressing.

In one embodiment, an example of which is illustrated in FIG. 6, the structural features may direct wound fluid flowing from the edges 125 of the wound bed 120, particularly the edges 626 of the fistula 122 toward the center of an absorptive dressing 601 to promote a pull of the tissues toward a midline of the fistula 122. The absorptive dressing 601 may have the physical and chemical properties of the various embodiments of absorptive dressings discussed herein, for example, the absorptive dressings 101, 501a, 501b and 501c. The absorptive dressing 601 may also include preformed flow paths 614 of large diameter pores through a scaffold 615 of small diameter pores to encourage wound fluid to primarily move through the preformed flow paths 614. The preformed flow paths 614 may include pores having one or more diameters different from the pore size(s) of the scaffold 615 (e.g., greater than the pore size of the scaffold) or may include hollow pathways, e.g., from the side of the absorptive dressing 601 closest to the wound bed 120 to the opposite side farthest from the wound bed 120. The preformed flow paths 614 may be arranged in an hourglass-like shape, such as an a top heavy hourglass shape as shown in FIG. 6, or the preformed flow paths 614 may have a symmetrical or bottom-heavy hourglass-like shape. The hourglass-like shape may be three-dimensional, such that a cross-section of the absorptive dressing 601 in a horizontal direction may show the preformed flow paths 614 as circles of different sizes corresponding to the level of the hourglass-like shape at which the cross-section is taken. In further embodiments, the preformed flow paths 614 may have a cone-shape, with the larger opening of the cone-shape facing the fistula 122. In such embodiments, the smaller opening or apex of the cone-shape may face the vacuum pump 134 located above it.

In some embodiments, more than one vacuum pump 134 may be included, for example, two to five vacuum pumps 134, at the upper ends 616 of the preformed flow paths 614. Alternatively, a vacuum pump capable of creating a circular negative pressure flow above the upper ends 616 of the preformed flow paths 614 can be used. The lower ends 617 of the preformed flow paths 614 may be positioned between the edges 626 of the fistula 122 so that the negative pressure of the vacuum pump 134 directs the fluid flow and the edges 626 of the fistula 122 inwardly to aid in the closure of the fistula 122. Prior to use, the absorptive dressing 601 may be cut in order to have the lower ends 617 of the preformed paths 614 correctly sit between the edges 626 of the fistula 122. Without being bound by theory, it is believed that in use, negative pressure created by the vacuum pumps 134 may pull both the wound fluid and the edges 626 of the fistula 122 upwards and because of the lower pressure of the preformed flow paths 614, the wound fluid and the edges 626 will be pulled towards the preformed flow paths 614. The directionality of the movement of the edges 626 will aid in the closure of the fistula 122. Further, as the edges 626 of the fistula 122 grow closer together, a further embodiment of the absorptive dressing 601 can be used in which lower ends of the preformed flow paths 614 are positioned closer together than in previously used absorptive dressing 601, so that the edges 626 of the fistula 122 are still being directed inwardly during the use of the vacuum pumps 134. This process can be repeated until the fistula is closed or until the edges of the fistula are too close together for preformed flow paths to create an inward pull.

In use, the absorptive dressing 601 including the preformed flow paths 614 may be applied to the wound bed 120 including the smooth muscle fistula 122. The absorptive dressing 601 may be positioned such that the lower ends 617 of the preformed flow paths 614 are between the edges 626 of the fistula 122. An occlusive material 130 may be overlaid on the absorptive dressing 601 such that it fully covers the edges 125 of the wound bed 120. Medical personnel may exert pressure on the occlusive material 130 until it adheres to the skin 124 and creates an airtight seal over the wound bed 120. The adapter 131 may be connected to a source of negative pressure, for example, a vacuum pump 134. The vacuum pump 134 may be assembled with the vacuum tube connector 132 and the vacuum tube 133 in order to connect to the adapter 131. However, more than one set of the vacuum pumps 134, vacuum tube connectors 132, the vacuum tubes 133 and adapters 131 may be assembled as shown in FIG. 6. The adapter 131 may be connected to the access point in the occlusive material 130 to allow negative pressure to flow from the vacuum pump 134 to the absorptive dressing 601. If more than one vacuum pump 134 is used, each adapter 131 associated with each vacuum pump 134 may have its own access point in the occlusive material 130. Upon activating the vacuum pump 134, negative pressure may be applied to the absorptive dressing 601 thereby withdrawing wound fluid from the absorptive dressing 601 and the wound bed 120. Without being bound by theory, negative pressure created by the vacuum pump or vacuum pumps 134 may pull both the wound fluid and the edges 626 of the fistula 122 upwards and towards the preformed flow paths 614.

Other embodiments, as shown in FIGS. 7A-7B, may include structural features that create pressure gradients and/or physical barriers to direct fluid flow. Such structural features may include barriers 770 composed of plastic, metal or other materials, such as biocompatible materials. However, because the barriers 770 may be incorporated into an absorptive layer 701 and not in direct contact with tissue, non-biocompatible materials may also be used. The absorptive dressing 701 may have the physical and chemical properties of the various embodiments of absorptive dressings discussed herein, for example, the absorptive dressings 101, 501a, 501b and 501c.

The barriers 770 may have a wing-like shape, such as an airplane wing-shape. For example, as shown in FIG. 9C, the barriers 770 may be asymmetrical along a chord line 771 connecting the leading edges 772 and the trailing edges 773 of the barriers 770 creating a camber in which the inner portions 774 of the barriers 770 have a thickness $t_1$ greater than the thickness $t_2$ of the outer portions 775 of the barriers 770. The inner portions 774 are directed towards an area of the absorptive dressing 701 above the center of the fistula 122 and the outer portions 775 are directed away from the area of the absorptive dressing 701 above the center of the fistula 122. The leading edges 772 may also have an angle of attack $\alpha$ relative to the direction of fluid flow 776 from the fistula 122. Without being bound by theory, it is believed that the wing-like shape of the barriers 770 and the angle of attack $\alpha$ take advantage of the Bernoulli Principle to create a pressure gradient in which the pressure between the inner portions 774 of the barriers 770 is lower than the pressure surrounding the outer portions 775 of the barriers 770. With the application of negative pressure from the vacuum pump 134, wound fluid flowing from the fistula 122 along with the edges 626 of the fistula 122 will be directed towards the area of low pressure between the inner portions 774, constricting the opening of the fistula and aiding in wound closure.

The barriers 770 may be a single piece structure or multiple pieces. For example, the barriers 770 may be a single and/or monolithic donut-shaped structure when viewed from above or the barriers 770 may be multiple overlapping wings arranged in a circle around the area above the fistula 122. In further embodiments, the barriers 770 may vary in size. Without being bound by theory, it is believed that by varying the size of the barriers 770, for example, incrementally from small to large around the circumference of the barriers 770, the directionality of the fluid flow can be controlled.

The barriers 770 may have a height from the leading edges 772 to the trailing edges 773 of about 5 mm to about 40 mm. In some embodiments, the barriers 770 may have a height from the leading edges 772 to the trailing edges 773 of about 10 mm to about 30 mm. The barriers 770 may have a width, including the thickness $t_1$ of the inner portions 774 and the thickness $t_2$ of the outer portions 775, of about 1 mm to about 10 mm. In some embodiments, the barriers 770 may have a width, including the thickness $t_1$ of the inner portions 774 and the thickness $t_2$ of the outer portions 775, of about 1 mm to about 3 mm.

In use, the absorptive dressing 701 including the barriers 770 may be applied to the wound bed 120 including the smooth muscle fistula 122. The absorptive dressing 701 may be positioned such that the leading edges 772 of the barriers 770 are above or between the edges 626 of the fistula 122. An occlusive material 130 may be overlaid on the absorptive dressing 701 such that it fully covers the edges 125 of the wound bed 120. Medical personnel may exert pressure on the occlusive material 130 until it adheres to the skin 124 and creates an airtight seal over the wound bed 120. The adapter 131 may be connected to a source of negative pressure, for example, a vacuum pump 134. The vacuum pump 134 may be assembled with the vacuum tube connector 132 and the vacuum tube 133 in order to connect to the adapter 131. The adapter 131 may also be connected to the access point in the occlusive material 130 to allow negative pressure to flow from the vacuum pump 134 to the absorptive dressing 701. Upon activating the vacuum pump 134, negative pressure may be applied to the absorptive dressing 701 thereby withdrawing wound fluid from the absorptive dressing 701 and the wound bed 120. Without being bound by theory, negative pressure created by the vacuum pump 134 may pull both the wound fluid and the edges 626 of the fistula 122 upwards and towards the area between the inner portions 774 of the barriers 770.

Further embodiments, examples of which are shown in FIGS. 8A-8D, may include structural features including suitable devices for drawing in wound fluid from the wound bed 120 in an upward and spiral pattern that may promote lifting and, at the same time, gentle twisting of the tissues in the wound bed 120. The lifting and twisting motion of the tissue as wound fluid is withdrawn through the device may further encourage the wound edges to be drawn together toward the midline of the wound bed 120 and promote ultimate wound closure. As shown in FIG. 8A, the structural features may include a radial housing 880 that may be incorporated into an absorptive dressing 801. The absorptive dressing 801 may have the physical and chemical properties of the various embodiments of absorptive dressings discussed herein, for example, the absorptive dressings 101, 501a, 501b and 501c. The radial housing 880 may be positioned such that a central axis C of the radial housing 880 is above the center of the fistula 122. The radial housing 880 may include a substantially hour-glass shaped hollow structure. Alternatively, the radial housing 880 may include one or more tubes spirally wound to form a cone-shaped structure where the larger opening of the cone-shaped structure faces the fistula 122. Without being bound by theory, it is believed that by virtue of its shape and structure, the radial housing 880 is capable of spinning a fluid moving through the radial housing 880 at a suitable pressure. The fluid may include a gas, a liquid or a combination of both. For example, the fluid may include filtered air and/or saline.

In some embodiments, the fluid may be delivered into the radial housing 880 under pressure through a delivery tubing 885, such as by an air compressor, or by creating a twisted Venturi effect where wound fluid moving through a central area 886 of the radial housing 880 draws gas though the delivery tubing 885 by a vacuum pressure. The radial housing 880 may include a radial tubing 881 that is capable of receiving the fluid from the adjacent delivery tubing 885. The fluid may then be delivered from the radial tubing 881 into the central area 886 of the radial housing 880 via injection ports 887. The central area 886 may be defined by the radial tubing 881 of the radial housing 880. The injection ports 887 may have varied diameters along the length and/or height of the radial housing 880 to promote the rotation and upward force of the wound fluid and resultant toroidal twist of the tissue. For example, the injection ports 887 may be larger at the inferior opening 882 and smaller at the flow constriction zone 883. Alternatively, the injection ports 887 may be smaller at the inferior opening 882 and larger at the flow constriction zone 883. In addition, the walls 888 of the injection ports 887 may be angled to direct the flow of the fluid. The walls 888 of the injection ports 887 may be angled such that the fluid is directed to the center of the central area 886.

In some embodiments, the radial housing 880 may include a single continuous radial tubing 881, as shown in FIG. 8B, or may include multiple pieces of radial tubing coupled together. The radial tubing 881 may include a flexible, biocompatible, and/or biodegradable material. For example, the radial tubing 881 may include a polymeric material where each layer of the radial tubing 881 may be flexible in relation to adjacent layers and/or may be flexible in relation to its contact with the wound bed 120 to provide for patient ambulation. In one embodiment, each layer of the radial tubing 881 may be offset as the radial tubing 881 ascends to achieve the hourglass shape. Accordingly, the radial housing 880 may include at least three blended zones, each of which may have a different diameter. For example, the three blended zones may include at least an inferior opening 882, a superior opening 884, and a flow constriction zone 883.

In some embodiments, the wound fluid may enter the central area 886 of the radial housing 880 from the wound bed 120 (including the smooth muscle fistula 122), through the inferior opening 882, and may exit the superior opening 884 to the vacuum pump 134. However, in some embodiments, the radial housing 880 may be symmetrical such that either the inferior opening 882 or the superior opening 884 may function as the fluid inlet or outlet. Accordingly, either end of the radial housing 880 may be applied to the wound bed 120. In such embodiments, as shown in FIG. 8C, the side of the radial housing 880 facing downward and touching the wound bed 120 may function as the inferior opening 882 and the side facing upward toward the vacuum source including the vacuum tube 133 may function as the superior opening 884.

In some embodiments, the delivery tubing 885 may have valves, for example, one-way valves, such as butterfly valves or valves similar in function and/or structure to a revolving door, for preventing a reversal of flow. In other embodiments, the radial housing 880 may have one-way valves at the delivery tubing 885 to prevent wound fluid from exuding up into the vacuum tube 133 or vacuum pump 134 after the vacuum pump 134 is turned off.

As also shown in FIG. 8C, in some embodiments, the walls 888 of the injection ports 887 may be angled such that the fluid is directed to the center of the flow constriction zone 883. However, for the injection ports 887 closest to the inferior opening 882, the injection ports 887 may be angled perpendicular to the central axis C of the radial housing 880 in order to push the fluid towards the central axis C of the radial housing 880 and resultantly push the edges 626 of the fistula 122 closer together.

In some embodiments, as shown in FIG. 8D, the walls 888 of the injection ports 887 may be angled in a circumferential direction. Without being bound by theory, it is believed that by angling the injection ports 887 in a circumferential direction, the fluid will be rotated in a helical pattern up the radial housing resulting in a toroidal twist of the fluid and of the edges 626 of the fistula 122 facilitating closure of the fistula 122.

In various embodiments of the present invention, the radial housing 880 may comprise a flexible, biodegradable material that may be compressed under the negative pressure provided by the vacuum pump 134. For example, the radial housing 880 may be made of a composition that can dissolve, such as sugar crystals and/or a chromic gut polymer. In some embodiments, one or more additives may optionally be applied to the inside of the radial housing 880 to interact with the wound fluid entering through the inferior opening 882. For example, the additives may optimize at least one of the adhesion or cohesion of the wound fluid as it travels through the radial housing 880 and may encourage the toroidal twist of the wound fluid. In some embodiments, additives may be added to facilitate or slow the rate of dissolution of the radial housing 880, depending the desired resulted in view of the characteristics of the fistula 112. For example, for a radial housing 880 made of sugar crystals, additives may be added to slow the rate of dissolution so that the dissolution of the radial housing 880 correlates with the rate of wound healing.

In some embodiments, the radial tubing 881 may taper in diameter toward the flow constriction zone 883. In other embodiments, the diameter of the radial tubing 881 may remain constant or may increase toward the flow constriction zone 883. The radial tubing 881 may have a diameter between about 0.5 mm and about 5 mm. The injection ports 887 may be circular in shape and have a diameter of about 0.1 mm to about 0.7 mm. However, the injection ports 887 need not be circular and may have any other geometric shape.

The radial housing may have a diameter at the inferior opening 882 sufficient to completely encircle the fistula 122. For a stomatized fistula, the radial housing may have a diameter at the inferior opening sufficient to completely encircle the fistula 122 including the stomatized walls surrounding the fistula. For example, the radial housing 880 may have a diameter of about 10 mm to about 40 mm. In some embodiments, the radial housing 880 may have a diameter of about 15 mm to about 25 mm.

In further embodiments, the radial tubing 881 of the radial housing 880 may be a single hourglass shaped structure. For example, the radial tubing 881 may include a double-walled structure that receives fluid from the delivery tubing 885 and have injection ports on the inner pane of the double-walled structure so that the fluid can enter the central area 886.

The delivery tubing 885 may be a single tube on one side of the radial housing 880, or it may be multiple tubes on opposite sides of the radial housing 880, as shown for example in FIGS. 8C-8D. The delivery tubing 885 may include two or more tubes spaced around the periphery of the radial housing 880. Alternatively, the radial housing 880 may be a double-walled hollow cylindrical structure surrounding the radial housing 880 and capable of delivering fluid around the entire circumference of the radial housing 880 at the inferior opening 882. The delivery tubing 885 may have a diameter similar to the radial tubing 881 of the radial housing 880. For example, the delivery tubing 885 may have a diameter between about 0.5 mm and about 5 mm.

In use, the absorptive dressing 801 including the radial housing 880 may be applied to the wound bed 120 including the smooth muscle fistula 122. The absorptive dressing 801 may be positioned such that the inferior opening 882 of the radial housing 880 encircles the fistula 122. An occlusive material 130 may be overlaid on the absorptive dressing 601 such that it fully covers the edges 125 of the wound bed 120. Medical personnel may exert pressure on the occlusive material 130 until it adheres to the skin 124 and creates an airtight seal over the wound bed 120. The adapter 131 may be connected to a source of negative pressure, for example, a vacuum pump 134. The vacuum pump 134 may be assembled with the vacuum tube connector 132 and the vacuum tube 133 in order to connect to the adapter 131. The adapter 131 may also be connected to the access point in the occlusive material 130 to allow negative pressure to flow from the vacuum pump 134 to the absorptive dressing 801. Upon activating the vacuum pump 134, negative pressure may be applied to the absorptive dressing 801 thereby withdrawing wound fluid from the absorptive dressing 801 and the wound bed 120. Without being bound by theory, negative pressure created by the vacuum pump 134 may pull both the wound fluid and the edges 626 of the fistula 122 upwards and towards the central area 886.

Referring to FIG. 9, in some embodiments of the present invention, a negative pressure treatment system 900 may further include a wound bed interface layer 902 between the absorptive dressing 101 and the wound bed 120. The interface layer 902 may be used with any of the embodiments of the absorptive dressings 101, 501a, 501b, 501c, 601, 701 and 801 described above. The wound bed interface layer 902 can be a healing layer having an affinity for living tissue and/or wound fluid produced by the wound. The interface layer 902 may form chemical interactions, such as chemical bonds and/or attractions, with the tissue in the wound bed 120 at the interface of the interface layer 902 and the wound bed 120. In one embodiment, the interface layer 902 may form a "chemical seal" where the chemical interactions effectively promote closure of the wound bed 120. Closure of the wound bed 120 may reduce or eliminate the flow of wound fluid out of the wound bed 120. For example, where the wound bed 120 includes an enteric fistula as the smooth muscle fistula 122, the flow of intestinal material out of the wound bed 120 may slow and ultimately stop due to the chemical seal.

In some embodiments, the interface layer 902 may provide normalization of negative pressure at the wound bed 120. The vertical distribution of negative pressure through the absorptive dressing 101 between the source of vacuum pressure at the occlusive material 130 and the bottom of the absorptive dressing 101 that contacts the wound bed 120 or the interface layer 902 may be variable depending on the thickness of the absorptive dressing 101. Application of the interface layer 902 between the absorptive dressing 101 and the wound bed 120 may enhance fluid management of exudate from the wound bed 120 by creating a uniform layer of negative pressure at the wound bed 120. The uniformity of pressure provided by the interface layer 902 may improve closure of difficult to close wounds such as stomatized wounds where the inner walls of the wound may become thickened and may resist closure.

In various embodiments, the interface layer 902 may be placed over the smooth muscle fistula 122 in the wound bed 120. The absorptive dressing 101 may then be placed over the interface layer 902. In various embodiments, the interface layer 902 may be at least partially coupled to the absorptive dressing 101. In some embodiments, the interface layer 902 may include an ester-based material, for example an ester-based material with the physical and chemical properties discussed above with regards to the absorptive dressing 101. In one embodiment, the interface layer 902 may include a bio-absorbable material. The bio-absorbable material may include a hydrophilic material that may have an affinity to the tissue of the smooth muscle fistula 122. In one embodiment, the bio-absorbable material may include a suture material such as absorbable surgical plain gut suture. Plain gut suture is composed of purified connective tissue and may absorb in the body within a few days by enzymatic dissolution as part of the body's response to a foreign object. In some embodiments, the bio-absorbable material may include a longer lasting absorbable material that dissolves more slowly than plain gut sutures, such as chromic gut sutures or Vicryl™. The ester-based material and/or the bio-absorbable material may resist tissue ingrowth from the smooth muscle fistula 122.

In another embodiment, the interface layer 902 may include a hydrophobic non-absorbable material. For example, the hydrophobic material may comprise a petroleum emulsion such as Adaptic® or a silicone wound dressing such as Mepitel®. Such hydrophobic material may also resist tissue ingrowth from the smooth muscle fistula 122.

In some embodiments, the interface layer 902 may be a thin sheet having a thickness. In one embodiment, the thickness may be about the thickness of a sheet of printer paper, such as about 100 μm. The interface layer 902 may include a plurality of pores to allow wound fluid produced by the wound bed 120 to flow through the interface layer 902 and into the absorptive dressing 101. The diameter of the pores may be similar to the width/diameter of smooth muscle cells, such as between about 1 μm to about 20 μm. In one embodiment, the interface layer 902 may include a single layer of pores. In some embodiments, the interface layer 902 may include more than one layer of pores where each layer includes a substantially uniform pore size and/or pore geometry within each layer, but a different pore size and/or pore geometry than an adjacent layer or layers. For example, the interface layer 902 may include a layer structure and/or pore structure as described with reference to the absorptive dressings 501a, 501b and 501c and FIGS. 5A-5C above. For example, the interface layer 902 may include multiple alternating layers in which the layers between layers of smaller pore size and larger pore size, such as discussed regarding FIGS. 5A-5B. In various embodiments, the smaller pores may be about 1 μm to about 10 μm and the larger pores may be about 10 μm to about 20 μm. In some embodiments, the interface layer 902 may include a layer with larger pores sandwiched between two smaller pore layers, such as described with reference to FIG. 5C. This configuration provides for a reversible interface layer 902 which may facilitate use by medical staff. The interface layer 902 may also have smaller pores interspersed between larger pores as described with respect to FIG. 5C above. Additionally, the interface layer 902 of this embodiment may include pores having a limited reticulation to reduce the volume and/or rate of wound fluid flow through the interface layer 902. In embodiments in with the interface layer 902 has multiple layers, the total width of all layers of the interface layer 902 combined may be about 100 μm. In some embodiments, the interface layer 902 may be a thin film or sheet having a thickness.

In use, the interface layer 902 may be applied to the wound bed 120 including the smooth muscle fistula 122 prior to application of any of the embodiments of the absorptive dressings 101, 501a, 501b, 501c, 601, 701 and 801 described above.

EXAMPLE 1

A female patient diagnosed with Crohn's disease was hospitalized having three enterocutaneous fistulas at the biliary junction. Various conventional treatments were attempted, but her fistulas persisted, having a fluid drainage rate of 1000-2000 ml per day. The patient was informed that her body would not heal this fistula on its own and was declared terminal. The patient agreed to an experimental procedure in which an ester-based foam was placed directly on the fistulas. The ester-based foam was composed of reticulated polyurethane ester foam with a pore size of 133-600 μm sold under the trade name V.A.C. VeraFlo Cleanse™ Dressing by Kinetic Concepts, Inc. The ester-based foam was felted such that the size of the pores varied directionally within the foam, where the pore size was greater along the length of the foam than along the direction of felting (i.e. the thickness). The foam was placed directly on the fistulas, with the width of the ester-based foam perpendicular to the fistulas and a flat surface of the ester-foam in direct contact with the fistula, covered with an occlusive material and attached to a vacuum pump via a vacuum tube, as exemplified in FIG. 1. A second vacuum tube and pump was positioned at the opposite end of the wound from the fistulas to collect exuded drainage fluid not collected by the first vacuum pump. The ester-based foam was replaced every three days. Within about 12 hours of the experimental procedure, the fluid drainage had decreased to a rate of approximately 500 ml/day. In the proceeding days, the fluid drainage decreased to approximately 200 ml/day. In addition, the overall coloration, texture and smell of the wound improved within three days. The tissue at the wound bed improved from a yellowish slough-covered tissue to a red, beefy granular tissue. In addition, likely do to the decrease in fluid drainage, the smell of bile at the wound site decreased within the first three days of the experimental procedure as well.

In the foregoing description, the invention has been described with reference to specific embodiments. Various modifications and changes may be made, however, without departing from the scope of the present invention as set forth. The description and figures are to be regarded in an illustrative manner, rather than a restrictive one and all such modifications are intended to be included within the scope of the present invention. Accordingly, the scope of the invention should be determined by the generic embodiments described and their legal equivalents rather than by merely the specific examples described above. For example, the steps recited in any method or process embodiment may be executed in any appropriate order and are not limited to the explicit order presented in the specific examples. Additionally, the components and/or elements recited in any system embodiment may be combined in a variety of permutations to produce substantially the same result as the present invention and are accordingly not limited to the specific configuration recited in the specific examples.

For example, while certain embodiments of the methods and systems described above disclose the withdrawal of body fluid without introducing any other fluid in order to promote healing, such embodiments may be modified to optionally introduce a carrier fluid such as air, water, saline, or other solutions or fluids into the wound to further encourage a desired flow of body fluid, and thereby promote healing.

Benefits, other advantages and solutions to problems have been described above with regard to particular embodiments. Any benefit, advantage, solution to problems or any element that may cause any particular benefit, advantage or solution to occur or to become more pronounced, however, is not to be construed as a critical, required or essential feature or component.

Other combinations and/or modifications of the above-described structures, arrangements, applications, proportions, elements, materials or components used in the practice of the present invention, in addition to those not specifically recited, may be varied or otherwise particularly adapted to specific environments, manufacturing specifications, design parameters or other operating requirements without departing from the general principles of the same.

The present invention has been described above with reference to specific embodiments. However, changes and modifications may be made to the above embodiments without departing from the scope of the present invention. These and other changes or modifications are intended to be included within the scope of the present invention.

The invention claimed is:

1. A method of treating a wound bed including a smooth muscle fistula without causing substantial cellular disruption or damage, the method comprising:
    applying an absorptive dressing comprising an ester-based foam having pores with a width of about 0.1 μm to about 80 μm directly to the wound bed including the smooth muscle fistula; and
    applying a negative pressure to the absorptive dressing to thereby withdraw wound fluid from the wound bed.

2. The method of claim 1, further comprising applying an occlusive material over the absorptive dressing to form a seal at the wound bed.

3. The method of claim 1, wherein the absorptive dressing comprises secondary structural features within the ester-based foam and adapted to impart a flow pattern to the wound fluid being withdrawn from the wound bed.

4. The method of claim 1, wherein the ester-based foam comprises at least two layers and wherein a first layer has an average pore size greater than an average pore size of a second layer.

5. The method of claim 1 wherein the ester-based foam has pores with a width of about 0.1 μm to about 50 μm.

6. A negative pressure treatment system for the treatment of a wound bed including a smooth muscle fistula, the negative pressure treatment system comprising:
    an absorptive dressing comprising an ester-based foam adapted to be placed directly against the wound bed and to contact smooth muscle without causing substantial cellular disruption or damage in the negative pressure environment, the foam having primary structural features comprising pores with a width of about 0.1 μm to about 50 μm and secondary structural features adapted to direct a flow of wound fluid from the wound bed;
    a vacuum pump configured to apply negative pressure to the absorptive dressing to thereby withdraw wound fluid from the wound bed; and
    an interface layer adapted to be placed between the absorptive dressing and the wound bed.

7. The negative pressure treatment system of claim 6, wherein the interface layer comprises an ester-based material.

8. The negative pressure treatment system of claim 7, wherein the interface layer comprises a film having pores with a width of about 0.1 μm to about 50 μm.

9. A negative pressure treatment system for the treatment of a wound bed including a smooth muscle fistula, the negative pressure treatment system comprising:
    an absorptive dressing comprising an ester-based foam layer;
    an interface layer adjacent to the absorptive dressing;
    wherein the absorptive dressing is adapted to be placed directly against the wound bed, and the interface layer is adapted for contacting smooth muscle without causing substantial cellular disruption or damage in the negative pressure environment, the foam having primary structural features comprising pores with a width of about 0.1 μm to about 50 μm and secondary structural features adapted to direct a flow of wound fluid from the wound bed; and
    a vacuum pump configured to apply negative pressure to the absorptive dressing to thereby withdraw wound fluid from the wound bed.

10. The negative pressure treatment system of claim 9, wherein the interface layer comprises an ester-based material.

11. The negative pressure treatment system of claim 10, wherein the interface layer comprises a film having pores with a width of about 0.1 μm to about 50 μm.

* * * * *